US006613956B1

(12) United States Patent
Klippel et al.

(10) Patent No.: US 6,613,956 B1
(45) Date of Patent: Sep. 2, 2003

(54) PI 3-KINASE FUSION MUTANTS AND USES THEREOF

(75) Inventors: Anke Klippel, San Francisco, CA (US); W. Michael Kavanaugh, Mill Valley, CA (US); Stephen D. Harrison, Berkeley, CA (US); Lewis T. Williams, Tiburon, CA (US)

(73) Assignee: Chiron Corporation, Emeryville, CA (US)

(*) Notice: Subject to any disclaimer, the term of this patent is extended or adjusted under 35 U.S.C. 154(b) by 0 days.

(21) Appl. No.: 08/832,571

(22) Filed: Apr. 2, 1997

Related U.S. Application Data

(60) Provisional application No. 60/033,470, filed on Dec. 19, 1996, provisional application No. 60/017,693, filed on May 14, 1996, and provisional application No. 60/015,387, filed on Apr. 4, 1996.

(51) Int. Cl.$^7$ .................. G01N 33/00; A01K 67/00; C07H 21/04; C12N 15/63
(52) U.S. Cl. .................. 800/3; 800/13; 536/23.1; 536/23.2; 536/23.4; 435/320.1; 435/455
(58) Field of Search .................. 800/2, 3, 13; 536/23.1, 536/23.2, 23.4; 435/325, 69.1, 15, 320.1, 455; 424/9.1, 9.2

(56) References Cited

FOREIGN PATENT DOCUMENTS

WO  PCT/US97/05573  4/1997

OTHER PUBLICATIONS

P Rodriguez–Viciana et al (1994) Nature; 370: 527–532.*
Whitman et al., "Type I Phosphatidylinositol Kinase Makes a Novel Inositol Phospholipid, Phosphatidylinositol–3–Phosphate" *Nature* 332:644–646, Apr., 1988.
Varticovski et al., "Activation of Phosphatidylinositol 3–Kinase in Cells Expressing abl Oncogene Variants" *Molecular and Cellular Biology* 11(2):1107–1113, Feb., 1991.
Aronheim et al., "Membrane Targeting of the Nucleotide Exchange Factor Sos is Sufficient for Activating the Ras Signalling Pathway" *Cell* 78:949–961, Sep., 1994.
Klippel et al., "Membrane Localization of Phosphatidylinositol 3–Kinase is Sufficient to Activate Multiple Signal–Transducing Kinase Pathways" *Molecular and Cellular Biology* 16(8):4117–4127, Aug., 1996.
Didichenko et al., "Constitutive Activation of Protein Kinase B and Phosphorylation of p47$^{phox}$ by a Membrane–Targeted Phosphoinositide 3–Kinase" *Current Biology* 6(10):1271–1278, Oct., 1996.
Reif et al., "Phosphatidylinositol 3–Kinase Signals Activate a Selective Subset of Rac/Rho–dependent Effector Pathways" *Current Biology* 6(11):1445–1455, Nov., 1996.
Klippel et al., "A Region of the 85–Kilodalton (kDa) Subunit of Phosphatidylinositol 3–Kinase Binds the 110–kDa Catalytic Subunit In Vivo" *Molecular and Cellular Biology* 13(9):5560–5566, Sep., 1993.
Klippel et al., "The Interaction of Small Domains Between the Subunits of Phosphatidylinositol 3–Kinase Determines Enzyme Activity" *Molecular and Cellular Biology* 14(4):2675–2685, Apr., 1994.
Hu et al., "Ras–Dependent Induction of Cellular Responses by Constitutively Active Phosphatidylinositol–3 Kinase" *Science* 268:100–102, Apr., 1995.
Kapeller and Cantley, "Phosphatidylinositol 3–Kinase" *BioEssays* 16(8):565–576, 1994.
Stephens et al., "Agonist–Stimulated Synthesis of Phosphatidylinositol (3,4,5)—Trisphosphate: a New Intracellular Signalling System" *Biochimica et Biophysica Acta.* 1179:27–75, 1993.
Hiles et al., "Phosphatidylinositol 3–Kinase: Structure and Expression of the 110 kd Catalytic Subunit" *Cell* 70:419–429, Aug., 1992.
Escobedo et al., "cDNA Cloning of a Novel 85 kd Protein that has SH2 Domains and Regulates Binding of P13–Kinase to the PDGF β–Receptor" *Cell* 65:75–82, 1991.
Buss et al., "Activation of the Cellular Proto–Oncogene Product p21 Ras by Addition of a Myristylation Signal" *Science* 243:1600–1603, 1989.
Kaplan et al., "Phosphatidylinositol Metabolism and Polyoma–Mediated Transformation" *Proc. Natl. Acad. Sci. USA* 83:3624–3628, Jun., 1986.
Schultz et al., "Amino Terminal Myristylation of the Protein Kinase p60src, a Retroviral Transforming Protein" *Science* 227:427–429, 1985.
Deichaite et al., "In Vitro Synthesis of pp60$^{v-src}$: Myristylation in a Cell–Free System" *Mol. Cell Biol.* 8(10):4295–4301, Oct., 1988.
Cadwallader et al., "N–Terminally Myristoylated Ras Proteins Require Palmitoylation or a Polybasic Domain for Plasma Membrane Localization" *Mol. Cell Biol.* 14(7):4722–4730, Jul., 1994.
Hay et al., "Expression of Baculovirus P35 prevents Cell Death in Drosphila" *Development* 120:2121–2129, 1994.
Kaufman et al., "Activated Drosophila Ras1 is Selectively Suppressed by Isoprenyl Transferase Inhibitors" *Proc. Natl. Acad. Sci. USA* 92:10919–10923, Nov., 1995.
Littlewood et al., "A Modified Oestrogen Receptor Ligand–Binding Domain as an Improved Switch for the Regulation of Heterologous Proteins" *Nucleic Acids Research* 23(10):1686–1690, 1995.

* cited by examiner

*Primary Examiner*—David Guzo
*Assistant Examiner*—Quang Nguyen
(74) *Attorney, Agent, or Firm*—Charlene A. Launer; Donald Pochopien; Robert P. Blackburn

(57) ABSTRACT

Polynucleotide constructs encoding growth factor independent catalytically active membrane targeted PI 3-kinase mutants useful for therapeutic and research purposes are described. In addition, a method for using the polynucleotide constructs to screen for inhibitors of PI 3-kinase, a method for making 3' phosphorylated inositol phospholipids, methods of reducing cell death after trauma, and methods of overcoming insulin resistance are described.

4 Claims, 1 Drawing Sheet

```
                              SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:1:

GCGCCCACCA TCATCACCAC CATTGAGTCG ACG                                33

(2) INFORMATION FOR SEQ ID NO:2:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:2:

GATCCGTCGA CTCAATGGTG GTGATGATGG TGG                                33

(2) INFORMATION FOR SEQ ID NO:3:

(i) SEQUENCE CHARACTERISTICS:
          (A) LENGTH: 5 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:3:

Asp Leu Gly Gly Ala
1               5

(2) INFORMATION FOR SEQ ID NO:4:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:4:

CGTCGCCATT TCTAAAGATG ATCTC                                         25
```

(2) INFORMATION FOR SEQ ID NO:5:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
TATGTCCCCC GTTCAGGTCC TCCTCGGAAA TCAGCTTCTG CTCATCCATT          50
```

(2) INFORMATION FOR SEQ ID NO:6:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
CTAGAATGGA TGAGCAGAAG CTGATTTCCG AGGAGGACCT GAACGGGGGA CA        52
```

(2) INFORMATION FOR SEQ ID NO:7:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Glu Gln Lys Leu Ile Ser Glu Glu Asp Leu
 1               5                  10
```

(2) INFORMATION FOR SEQ ID NO:8:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
GCATTCTCAC ATGATCACGC ACTTGGTCTT GGACTTCTTC TTCTTCTTTT TGCCATCTTT    60

GGAGGCGCCG AGCTCGTTCA AAGCATCCTG                                   90
```

(2) INFORMATION FOR SEQ ID NO:9:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
GGATCCTCAG CTCAGCACGC ACTTGCAGCT CATGCAGCCG GGGCCGCTGC TGGCGCCCCC    60

GAGCTCGTTC AAAGCATGCT G                                            81
```

```
(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CTGAGCAAGA AGCTTTGG                                                          18

(2) INFORMATION FOR SEQ ID NO:11:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

TATGTCCCCC GCGCTGGCTG GGGTCCTTGG TCGTCTTGCT GCTCCC                            46

(2) INFORMATION FOR SEQ ID NO:12:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

CATGGGGAGC AGCAAGAGCA AGCCCAAGGA CCCCAGCCAG CGCGGGGAC A                       51
```

PI 3-KINASE FUSION MUTANTS AND USES THEREOF

This application claims priority based upon provisional application No. 60/033,470, filed Dec. 19, 1996; provisional application No. 60/017,693, filed May 14, 1996; and provisional application No. 60/015,387, filed Apr. 4, 1996, all now abandoned.

GENERAL DESCRIPTION

1. Field of the Invention

This invention provides polynucleotide constructs encoding constitutively active membrane-targeted PI 3-kinase mutants, methods for making polynucleotide constructs, an in vivo method for screening for inhibitors of PI 3-kinase using the constructs, use of the polynucleotide constructs to prevent cell death, or to restore insulin responsiveness in type II diabetes, use of the polynucleotide constructs to express PI 3-kinase mutants that generate 3' phosphorylated inositol phospholipids, and use of these phospholipids to prevent cell death.

2. Background of the Invention

Phosphotidylinositol (PI) 3-kinase, both a phospholipid kinase, and a protein serine/threonine kinase, is implicated in certain oncogenic or mitogenic responses. See Carpenter et al., *Mol. Cell. Biol.* 13:1657–1665 (1993), Cantley et al., *Cell* 64:281–302 (1991), Escobedo and Williams, *Nature* 335:85–87 (1988), and Fantl et al, *Cell* 69: 413423 (1992). It is an intracellular heterodimer consisting of an 85-kDa regulatory subunit (p85), and a 110-kDa catalytic subunit (p110) that is stimulated by growth factors. See Whitman et al., *Nature* 332:644–646 (1988). The p85 subunit contains several domains and links the catalytic subunit to activated growth factor receptors. The cDNA for the p110 subunit has recently been cloned and expressed in insect and mammalian systems as described in Hiles et al., *Cell* 70:419–429 (1992). The general structure and function of PI 3-kinase, including analysis of the structure and function of its subunits p85 and p110, are described in Klippel et al., *Mol. Cell. Biol.* 13:5560–5566 (1993), and in Klippel et al., *Mol. Cell. Biol.* 14:2675–2685 (1994).

The p85 subunit of PI 3-kinase has several domains, including a 200 amino acid region of p85 located between the two SH2 domains. This domain, called the inter-SH2 or iSH2 domain, has been found sufficient to promote interaction with p110 in vivo with activity comparable to that of full-length p85. See Klippel et al., *Mol. Cell. Biol.* 13:5560–5566 (1993). Additionally, a complex between a 102 amino acid segment of p85 and the p110 subunit has been found to be catalytically active, as described in and Klippel et al., *Mol. Cell. Biol.* 14:2675–2685 (1994).

Previously, studies to elucidate the of PI 3-kinase activation have been conducted by constructing receptor mutants to alter the signal transduction of PI 3-kinase, or by constructing mutant oncogenes to study a PI 3-kinase inducible oncogenic response. It would be advantageous to study effects of PI 3-kinase activation directly, without growth factor activation, so as to identify the role of PI 3-kinase in oncogenesis, mitogenesis, and other tyrosine kinase and PI related functions. Methods and compositions derived from such knowledge and use of PI 3-kinase to control oncogenesis or mitogenesis, would be advantageous in the treatment of cancer. In addition, it would be advantageous to develop methods and compositions for such applications as preventing cell death or treating type II diabetes.

SUMMARY OF THE INVENTION

In one aspect, the invention provides polynucleotide sequences comprising the p110 subunit of PI 3-kinase polynucleotide attached to a cell membrane targeting sequence. More specifically, the invention provides a polynucleotide sequence comprising a first nucleotide sequence encoding the p110 subunit of PI 3-kinase protein, or a derivative or mutant of this sequence having a single or multiple nucleotide substitution, deletion or addition, this derivative or mutant having p110 catalytic activity, and a second nucleotide sequence encoding a cell membrane targeting sequence, this second nucleotide sequence being attached to the first nucleotide sequence at the latter's 5' or 3' end. Further, the polynucleotide sequence of the invention can be structured so that the first nucleotide sequence also includes a nucleotide sequence encoding the p85 subunit of PI 3-kinase or a fragment of the p85 subunit, for example the iSH2 domain of the p85 subunit, capable of binding the p110 subunit. The cell membrane targeting sequence is a nucleotide sequence encoding a myristoylation, or a palmitoylation and farnesylation amino acid sequence.

Other aspects of the invention include methods of screening for inhibitors of PI 3-kinase, methods of making 3' phosphorylated inositol phospholipids, and the 3' phosphorylated inositol phospholipid produced thereby, and methods for activating enzyme effectors of PI 3-kinase having a pleckstrin homology domain.

Therapeutic aspects of the invention include methods of reducing cell death due to trauma, by administering to the cell a viral or non-viral vector including a polynucleotide sequence of the invention, or by administering a 3' phosphorylated inositol phospholipid to the cell. Another aspect of the invention is a method of promoting activation of an insulin signaling pathway by contacting a cell characterized by insulin resistance with a vector having a polynucleotide sequence of the invention.

DETAILED DESCRIPTION

Figure 1:
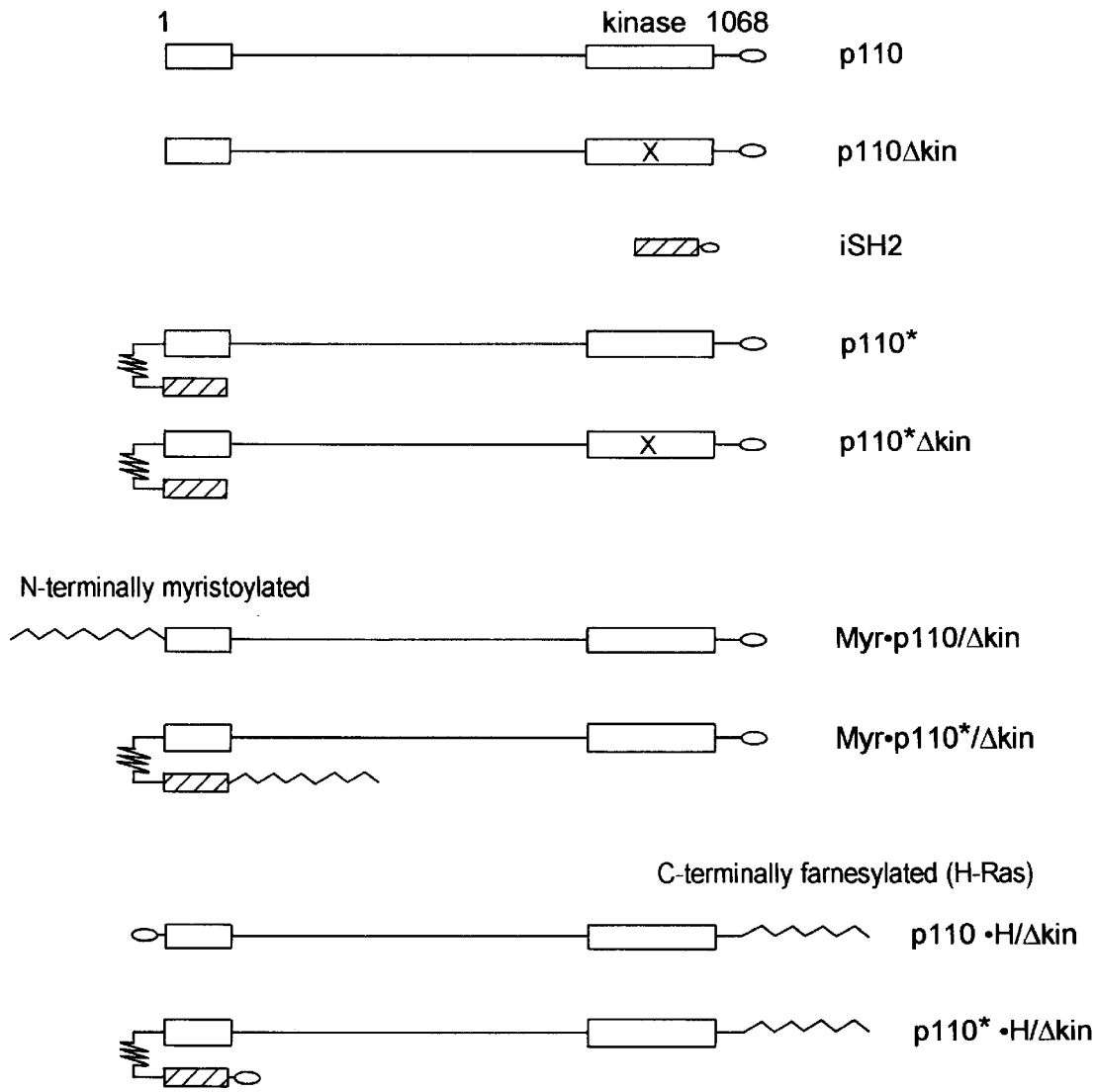
FIG. 1 is a schematic representation of polynucleotide sequences used in the Examples wherein the polynucleotide sequences derived from wild-type p110-encoding polynucleotide sequences are represented by open boxes with the catalytic domain of protein kinases depicted by a box labeled "kinase." The domain responsible for interaction with the iSH2 domain of the p85 subunit is shown as a small box at the p110 N-terminus. p110ΔKin is a kinase-deficient p110, containing a mutation within the catalytic domain at position 802 as indicated by an asterisk. The iSH2 domain (residues 468–567) of p85 that is required for PI 3-kinase catalytic activity is represented by a hatched bar. The first and last amino acids are numbered with respect to their position in the wild-type p85 or p110 sequence. p110* is a constitutively active chimera that contains the iSH2 domain of p85 attached to the N-terminus of p110 via a flexible "glycine linker." The p110*Δkin is the kinase-deficient version of p110*. Myr-p110 and Myr-p110*, as well as their kinase deficient versions, were modified at their respective N-terminal ends with the myristoylation sequence of pp60 c-Src. The C-terminal ends of p110-H and p110*-H and their kinase-deficient versions were extended by the farnesylation and palmitoylation sequences of H-Ras.

All patents, patent publications, and scientific articles cited herein are hereby incorporated by reference.

The Polynucleotide Constructs

Provided here are polynucleotide constructs encoding constitutively active forms of PI 3-kinase mutants. The polynucleotide constructs encoding PI 3-kinase fusion mutants are capable of inducing PI 3-kinase dependent signaling responses that are higher than those previously achieved with an equal or greater concentration of other PI 3-kinase mutants, due to the addition of one or more membrane targeting sequences. The term "PI 3-kinase mutant" or "PI 3-kinase fusion mutant" is a polypeptide sequence that differs from the native, full length PI 3-kinase sequence. Fusion mutant refers to a sequence encoding a PI 3-kinase sequence or portion of a PI 3-kinase sequence (including, for example, fused portions of PI 3-kinase subunits) fused to a cell membrane targeting sequence. PI 3-kinase is described in Kapeller and Cantley, *Bioessays* 16:565–576 (1994), and in Stephens et al., *Biochim. Biophys. Acta.* 1179:27–75 (1993). The p110 subunit of PI 3-kinase can be used to make the fusion mutants, including also all or a portion of the p85 subunit. In addition, single or multiple deletions, substitutions or additions of nucleic acids can be made to the p110 or p85 sequences, and the construct can be tested for retention of the desired function as described in Examples 2, 3, and 6 below. PI 3-kinase mutants of p85 are described, for example, in Klippel et al., *Mol. and Cell. Bio.* 13:5560–5566 (1993) and mutants of p110, including p110*, are described, for example, in Hu et al., *Science* 268:100–102 (1995). The native polynucleotide sequence of the p110 subunit, and the native polypeptide sequence it encodes are described in Klippel et al, *Mol. Cell. Biol.* 14: 2675–2685 (1994). It is on deposit with Genbank, accession number U03279. The native polynucleotide sequence of the p85 subunit of PI 3-kinase and the native polypeptide sequence it encodes are described in Escobedo et al., *Cell* 65:75–82 (1991). It is on deposit with Genbank, accession number M60651.

The invention provides a polynucleotide that comprises a first nucleotide sequence encoding the p110 subunit of PI 3-kinase protein, or a sequence encoding a derivative or mutant of the p110 subunit including single or multiple nucleotide substitutions, deletions or additions, this derivative or mutant having p110 subunit catalytic activity. The polynucleotide also comprises a second nucleotide sequence encoding a cell membrane targeting sequence that is attached to the 5' or 3' end of the first nucleotide sequence. Thus, the invention provides a polynucleotide that upon expression is targeted to the cell membrane.

In another aspect, the invention provides that the first polynucleotide sequence can further comprise a nucleotide sequence encoding the p85 subunit of PI 3-kinase protein or a sequence encoding a derivative or mutant of the p85 subunit including a single or multiple nucleotide substitution, deletion or addition, this derivative or mutant capable of binding the p110 subunit. The sequence encoding the p85-derived sequence can be a sequence encoding the amino acid sequence between the two SH2 domains of the p85 subunit, the inter-SH2 domain (iSH2) that is capable of binding the p110 subunit. An example of such a fusion molecule is p110* described below which incorporates the iSH2 domain of p85 into a construct containing a catalytically active p110 subunit, described in Hu et al., *Science* 268:100–102 (1995). To this fusion molecule, the cell membrane targeting sequence or sequences are added at the 5' or 3' end or both of the polynucleotide construct. The p110* fusion mutant also contains a linker region between the p85 and p110 sequences. The linker nucleotide sequence encoding the linker can comprise, for example, a sequence encoding a glycine rich region.

Thus, the PI 3-kinase mutant that is targeted to the membrane of a cell can be any p110-derived PI 3-kinase mutant that retains p110 kinase activity, including, for example, the p110 subunit of PI 3-kinase, and biologically active variations thereof, including but not limited those described in Klippel et al., *Mol. Cell Biol.* 13:5560–66 (1993), Klippel et al., *Mol. Cell Biol.* 14:2675–2685 (1994). The PI 3-kinase mutant can also be a constitutively active PI 3-kinase mutant such as p110* which can be constructed as described in Hu et al., *Science* 268:100–102 (1995). P110* includes the additional p85 derived sequence iSH2. The membrane targeting sequences for attachment at the polynucleotide level (i.e. at the 5' or 3' end) can include sequences encoding myristoylation or farnesylation and palmitoylation sequences. Generally, the farnesylation and palmitoylation sequences are used together at the same end of the polynucleotide sequence that is to be targeted to the membrane.

The PI 3-kinase mutants expressed from the polynucleotides of the invention promote "constitutive activity" which refers to the ability of the PI 3-kinase mutant to catalytically activate downstream effectors in the absence of growth factor stimulation. Thus, the fusion mutants demonstrate a growth factor independent induction of the downstream effectors of PI 3-kinase activity, or a catalytic activity, including but not limited to, for example, induction of pp70 S6 kinase and AKT kinase activities, and generation of active phosphoinositol 3' phosphorylated phospholipids. These improved membrane targeted PI 3-kinase mutants have increase utility: with only a small amount of mutant, in the absence of growth factor, greater amounts of PI 3-kinase catalytic activity are demonstrated.

The cell membrane targeting sequence of the fusion mutant can be any sequence that targets a protein to the membrane of a cell. The polynucleotide constructs of the invention have a nucleotide sequence encoding cell membrane targeting sequences attached to the 5' or 3' end of the polynucleotide construct. In the expressed proteins of the invention, the membrane targeting sequence thus may be located at the N-terminal or the C-terminal end. Also, membrane targeting sequence may be encoded in the polynucleotide sequence that encodes the mutant or a polypeptide cell membrane targeting sequence may be added to the expressed mutant at the N or C terminus by post translational modification. Exemplary membrane targeting sequences include myristoylation sequences, such as those described in Buss et al., *Science* 243:1600–03 (1989), Kaplan et al., *PNAS USA* 83:3624–3628 (1990), Schultz et al., *Science* 227:427429 (1985), and Deichaite et al., *Mol. Cell Biol* 8:4295–301 (1988), and farnesylation sequences and a palmitoylation sequences, such as those described in Cadwallader et al., *Mol. Cell Biol.* 14:4722–4730 (1994). Preferably a myristoylation sequence is added to the 5' end of a polynucleotide construct or to the N-terminus of an expressed polypeptide. Preferably, a farnesylation sequence is added to the 3' end of a polypeptide construct or to the C-terminus of an expressed polypeptide. Depending on whether the farnesylation sequence is derived from H-Ras or K-Ras, the farnesylation sequence is most preferably added in conjunction with either a palmitoylation sequence or a polybasic region of several lysines, as described in Example 1. The mutant polynucleotide may also contain both a myristoylation and a farnesylation sequence with either a palmitoylation or a polybasic sequence (chosing a palmitoylation or polybasic sequence depending on the protein from which the farnesylation sequence is derived) also as described in Example 1. Other mechanisms for creating a cell membrane targeted fusion mutant exist, including, but not limited to, for example, the addition of lipid moieties to the polypeptide once it has been expressed that act as cell membrane targeting sequences.

Nucleotide sequences encoding derivatives or mutants of the p110, p85, or cell membrane targeting sequences can have 50%, more preferably 60%, more preferably 70%, more preferably 80%, more preferably 90%, most preferably 95% nucleic acid sequence identity to a native sequence from which the derivative or mutant sequence is derived. For example, a polynucleotide sequence can include a nucleotide sequence encoding a sequence derived from the p110 subunit having 95% nucleic acid sequence identity to the native p110 nucleotide sequence, a nucleotide sequence encoding a sequence derived from the p85 subunit having 80% nucleic acid sequence identity to the native p85 nucleotide sequence, and a nucleotide sequence encoding a myristoylation sequence having 95% nucleic acid sequence identity to the native myristoylation sequence.

The intracellular polypeptides expressed upon expression of the polynucleotides of the invention in a host cell can have 60%, more preferably 70%, more preferably 80% more preferably 90% and most preferably 95% sequence identity to the native amino acid sequences of the particular PI 3-kinase subunit sequences and cell membrane targeting sequences comprising the entire polynucleotide construct. Thus, for example, a cell membrane targeted p110* sequence can contain within its intracellular expression product an iSH2 sequence of 90% amino acid sequence identity to the native iSH2 sequence cited, 95% amino acid sequence identity to the native p110 sequence, and 90% amino acid sequence identity to the native myristoylation sequence.

The polynucleotide constructs are made by first constructing the p110 polynucleotide sequence. To the p110 subunit-derived polynucleotide sequence is added a cell membrane targeting modification. Alternatively, a p85 derived polynucleotide sequence can be attached to the p110 subunit sequence, for example using a linker at the 5' end of the p110 sequence. To this fusion a membrane targeting sequence can then be attached. In all cases, attachment of nucleic acid sequences can mean fusion or ligation, for example, using standard molecular biology techniques. The cell membrane targeting sequence can be encoded in a polynucleotide sequence that is attached to the polynucleotide sequence encoding the sequence that it will modify. The membrane targeting sequence may also be a sequence added to the mutant polypeptide after the polypeptide has been expressed, such as, for example, a lipid moiety or lipid modification of the expressed polypeptide, or an expressed cell membrane targeting sequence. The membrane targeting sequence, whether encoded in the polynucleotide, or whether added after translation of the polypeptide, may be attached to the mutant at any position in the mutant that will target the mutant to a cell membrane.

These and all other polynucleotides of the invention can be assayed for function as described in Example 3 below.

Polynucleotide constructs can be made for the expression of fusion mutants with regulatable activity include the coding region for the respective molecule downstream of a CMV of SRα promoter and a viral translation initiation region. The p110 coding region can be attached at its 5' terminus to a mutant form of the regulatory domain of the mouse estrogen receptor, as described in Example 5. The regulatory domain of the mouse estrogen receptor comprises amino acids 281 to 599 and can be preceded by two or more glycine residues at the junction to the p110 sequence to provide for flexibility and for proper folding of the individual portions of the chimeric molecule. The estrogen receptor portion carries a mutation, GR525, which provides for the following characteristics: the GR525 mutation renders the fusion protein tightly dependent on 4-OHT and totally unresponsive to estrogen. These characteristics ensure a tightly regulated, nonleaky, induction of PI-3 kinase activity in response to 4-OHT.

On the same polynucleotide construct, can be located a TATA box domain and a virally derived translation initiation site. The translational initiation domain can be, for example, derived from the translational initiation domain from the SV40 large T antigen regulatory regions or from the Herpes Simplex thymidine kinase regulatory regions. These sequences can then be followed by the polynucleotide sequence encoding polynucleotide mutant of the invention. Expression ensues in an inducible fashion much as described in Littlewood et al., *Nucleic Acids Research* 23:1686–1690 (1995) with the additional advantage that the mutant is efficiently translated to result in a functional kinase mutant. As far as these inventors are aware, efficient expression and translation of PI 3-kinase or of PI 3-kinase mutants has not been achieved prior to this, and is advantageously achieved using the inducible expression method of the invention.

A polynucleotide construct for inducible expression of a mutant PI 3-kinase is also included in the invention. The construct includes a polynucleotide sequence encoding the following domains described 5' to 3': a binding site for a repressor protein, a TATA box, a viral sequence sufficient for efficient initiation of translation, and a polynucleotide sequence encoding a PI 3-kinase mutant. This construct can be used to inducibly express the polynucleotides of the invention, and generate useful products of the resulting activated pathways. The polynucleotide construct of the inducible expression system can have a binding site that can bind a chimeric protein having a DNA binding domain of a repressor protein and a transactivating domain of a different gene activator.

The term "repressor protein" refers to that class of proteins characterized by both an ability to bind DNA and alter transcription, and by the repression of transcription that results from this binding. Repressor proteins include, for example, the lac repressor, the tet repressor, the lambda repressor, and others as described in *Molecular Biology of the Cell*, Alberts et al. ed., Garland Press, New York, pp. 407, 420–426 (1994). The term "viral sequence sufficient for initiation of translation" as used herein refers to a polynucleotide sequence identified in a viral genome that functions to regulate translation, and which has been identified as controlling and facilitating the initiation of translation of viral proteins and which can be included for expression of heterologous proteins to facilitate initiation of translation of heterologous proteins. Such a region can, for example, be derived from the herpes simplex thymidine kinase, tk, gene for optimal initiation of translation region (hereafter "the tk upstream region"). This region can be isolated from plasmid pCG, described in Giese et al., *Genes and Development* 9:995–1008 (1995), which is a pEVRF derivative, described in Matthias et al., *Nucleic Acids Res.* (1989) 17:6418. Other such viral initiation of translation regions exist, including for example, the SV40 virus large T antigen initiation of translation region. The term "transactivating domain" as used herein refers to the domain of a gene regulatory protein such as, for example, those gene regulatory proteins described in *Molecular Biology of the Cell*, Alberts et al ed., Garland Press, New York, pp. 407, 420–426 (1994), also including, for example, the transactivating domain of VP16 as described in Gossen et al, *Science* 268: 1766–1769 (1995).

This domain of the gene activator molecules have the ability to activate transcription. In a preferred embodiment the transactivating domain can be VP16, the binding site can be a multimer, the DNA binding domain can have binding sites for Tet or Lac, and the repressor protein can be Tet or Lac.

The polynucleotide constructs of the invention, once designed, can be constructed by standard recombinant DNA technology and manipulation. For example, polynucleotide constructs having deletions, mutations, substitutions, fusions, and which otherwise encode polypeptide variants, derivatives, mutants, analogues, or chimeras can be constructed by conventional techniques of molecular biology, microbiology, and recombinant DNA technology that are within the skill of the art. The polynucleotide can be placed into a vector construct that directs its expression. The vector construct must include transcriptional promoter element(s), and preferably includes a signal that directs polyadenylation. In addition, the vector construct must include a sequence which, when transcribed, is operably linked to the sequence(s) or gene(s) of interest and acts as a translation initiation sequence.

Such techniques for polynucleotide and polypeptide construction and expression are explained fully in the literature, for example in Sambrook, et al. MOLECULAR CLONING; A LABORATORY MANUAL, SECOND EDITION (1989); DNA CLONING, VOLUMES I AND II (D.N Glover ed. 1985); OLIGONUCLEOTIDE SYNTHESIS (M. J. Gait ed, 1984); NUCLEIC ACID HYBRIDIZATION (B.D. Hames & S. J. Higgins eds. 1984); TRANSCRIPTION AND TRANSLATION (B. D. Hames & S. J. Higgins eds. 1984); B. Perbal, A PRACTICAL GUIDE TO MOLECULAR CLONING (1984); the series, METHODS IN ENZYMOLOGY (Academic Press, Inc.). Further, sequences that encode the above-described genes may also be synthesized, for example, on an Applied Biosystems Inc. DNA synthesizer (e.g., ABI DNA synthesizer model 392 (Foster City, Calif.)). Additionally, the polynucleotides can be constructed and cloned as described in PCR PROTOCOLS, Cold Spring Harbor, N.Y. 1991. The desired gene can also be isolated from cells and tissues containing the gene, using phenol extraction, PCR of cDNA, or genomic DNA. The gene of interest can also be produced synthetically, rather than cloned, as described in Edge, *Nature* 292: 756 (1981), Nambair et al., *Science* 223:1299 (1984), and Jay et al., *J. Biol. Chem.* 259:6311 (1984). Additionally, variations of any polynucleotide or polypeptide can be made by conventional techniques, including PCR or site-directed mutagenesis. The DNA constructs so synthesized can be ligated to an expression plasmid containing an appropriate promoter for expression in a desired host expression system. The host system can be in vitro, in vivo or ex vivo.

The polynucleotides of the invention can be used to transform host cells and can thus be expressed in these cells. Host cells appropriate for this transformation include bacterial, yeast, insect, or mammalian host cells, for example, including those host cells systems described in WO 96/35787. The polynucleotides can be used to stably transform cells in order to construct stable cell lines.

The Phospholipids and Methods for Making Them

The invention provides a method for making a 3' phosphorylated inositol phospholipid in vitro. In step one of the method vesicles containing PI-3 kinase phospholipid substrates, including for example, phosphatidylinositol (PI), phosphatidylinositol 4 phosphate (PI4P) and/or phosphatidylinositol 4,5 bisphosphate (PI4,5P$_2$,) are incubated with a PI 3-kinase mutant to generate 3' phosphorylated inositol phospholipid products from each substrate. In step 2 the reaction product is collected.

In the particular case where substrate comprises phosphatidylinositol 4,5 bisphosphate (PI4,5P$_2$,), the 3' phosphorylated inositol phospholipid generated will be phosphatidylinositol 3,4,5 trisphosphate (PI3,4,5P$_3$,). In this particular case, the phosphatidylinositol 3,4,5 trisphosphate (PI3,4,5P$_3$,) can be contacted prior to the collection step with a signaling inositol polyphosphate 5' phosphatase (SIP) polypeptide in order to generate phosphatidylinositol 3,4 bisphosphate (PI3,4P$_2$,), which is then collected. SIP is described in Egan et al, *Nature* 363:45–51 (1993), Zhang et al., *Proc. Natl. Acad. Sci. USA* 92:48534856 (1995), and York et al., *J. Mol. Biol.* 236:584–589 (1994).

Thus, the invention includes a method of making a 3' phosphorylated inositol phospholipid comprising contacting a polynucleotide sequence of the invention with a PI3 kinase substrate selected from the group consisting of phosphatidylinositol (PI), phosphatidyl 4-phosphate (PI4P) and phosphatidylinositol 4,5 bisphosphate (PI4,5,P$_2$), and isolating a 3' phosphorylated inositol phospholipid. Another aspect of the invention is that the 3' phosphorylated inositol phospholipid phosphatidylinositol 3,4,5 trisphosphate (PI3,4,5P$_3$,) is isolated. In some circumstances it may be to advantage contact the phosphatidylinositol 3,4,5 trisphosphate (PI3,4,5P$_3$,) with a signaling inositol polyphosphate 5' phosphatase (SIP) polypeptide to facilitate isolating phosphatidylinositol 3,4 bisphosphate (PI3,4P$_2$,).

Treatment of PI3,4,5P$_3$ with the inositol polyphosphate 5' phosphatase SIP leads to activation of Akt in vitro. This activation can thus be used as an assay to indicate whether the 3,4 inositol polyphosphate has been synthesized, and is described in more detail below.

The most effective way of making 3' phosphorylated inositol phospholipid is an intracellular method. A cell is transformed with a polynucleotide construct of the invention, and this host cell is used to express the polynucleotide and generate 3' phosphorylated inositol phospholipids from substrates naturally occurring in the cell. Because there is an excess of these substrates in cells, a constitutively active mutant such as embodied in any of polynucleotides of the invention will generate a large amount of 3' phosphorylated inositol phospholipids as compared to cell expressing native PI 3-kinase. These phospholipids, so generated, can be isolated or used within the cell for purposes such as those described herein.

Use of the Polynucleotide Compositions

The cell membrane targeted polynucleotide fusion mutants of the invention are useful for many applications. The polynucleotide constructs are useful in a research context for identifying and studying cellular processes by PI 3-kinase, without the need for prior growth factor activation. The use of polynucleotide constructs of the invention facilitates testing whether PI 3-kinase activation alone is sufficient for the induction of a signaling event.

The signaling events that can be tested for dependence on PI 3-kinase activation include, for example, many of the cellular responses that appear to be regulated by PI 3-kinase, including mitogenesis and oncogenesis; the reorganization of actin cytoskeleton as described in Kapeller et al., *Mol. Cell Biol.* 13:6052–6063 (1993); receptor internalization; histamine secretion; neutrophil activation; platelet activation as described in Zhang et al, *J. Biol. Chem.* 267:4686–4692 (1992); cell migration; glucose transport and antilipolysis;

and vesicle sorting as described in Stack et al., *EMBO J.* 12:2195–2204 (1993). Thus, the polynucleotides can be used for functional studies of PI 3-kinase activation in a variety of applications, including but not limited to study of the PI 3-kinase dependent effects of reorganization of actin cytoskeleton, receptor internalization, histamine secretion, neutrophil activation, platelet activation, cell migration, glucose transport and antilipolysis, vesicle sorting, apoptotic rescue, mitogenesis, and oncogenesis.

Further, studies of PI 3-kinase activation can be facilitated by using the membrane targeted polynucleotides for elucidating whether a particular PI 3-kinase dependent effect is due to a lipid phosphorylation event or a protein phosphorylation event, or both, by, for example, demonstrating the accumulation of a PI 3-kinase downstream effector in the presence of a polynucleotide of the invention.

The invention also includes an expression system for inducibly expressing the polynucleotides of the invention, as described above. The expression system is useful for conducting in vivo studies by, for example, overexpressing the polynucleotides of the invention, accumulating PI 3-kinase activation products for studies relating to the PI 3-kinase pathway, studying PI 3 kinase involvement in a particular cellular response in which PI 3-kinase is implicated, and screening for inhibitors of PI 3-kinase activity. The expression system is useful for study of PI 3-kinase function by stable expression in mammalian cells rather than by transient overexpression surmounting a previous problem in the art, that was the difficulty of expressing p110-derived subunits in a stable manner. This inducible system combines the system of post-translational activation by 4-hydroxy tamoxifen in mammalian cells, described, for example, in Littlewood et al., *NAR* 23:1686–1690 (1995), and the 5' upstream translation initiation site of a virus to accomplish an inducible expression of any of the polynucleotides of the invention. The viral translation initiation site can be derived from, for example, the Herpes Simplex virus thymidine kinase (TK) gene or the SV40 virus large T antigen gene. Finally, the invention provides a method for screening for inhibitors of PI 3-kinase using a transgenic fly expressing a polynucleotide of the invention under the control of an eye specific promoter. The eye tissue specific expression of the PI 3-kinase mutant results in a morphological change in the eye of the fly. This variant morphological change can revert to a wild type morphology upon administration to the fly of an inhibitor of PI 3-kinase. The transgenic fly screen for inhibitors of PI 3-kinase can be used as a primary screen for inhibitors of PI 3-kinase, or as a secondary screen for inhibitors that appear to inhibit PI 3-kinase in an in vitro or cell-based assay.

The cell membrane targeted polynucleotides of the invention may be used in a transgenic assay to screen for inhibitors of PI 3-kinase activity. The screening assay is conducted by feeding the flies food containing a candidate inhibitor. If the inhibitor is functional, the eye morphology reverts from mutant to wild-type. The candidate inhibitor can be a small molecule, including a small organic molecule, a peptide, a peptoid, a ribozyme or an antisense polynucleotide, for example. This screening assay can be applied to screening for inhibitors of any kinase capable of generating a mutant phenotype when expressed in the eye tissue under control of an eye-specific promoter.

Another embodiment of the invention is a method of screening for an inhibitor of PI 3-kinase activity by providing a transgenic insect expressing a polynucleotide of the invention under the control of an eye-specific promoter, resulting in a mutant eye morphology, administering to the transgenic insect a candidate inhibitor, and identifying a functional inhibitor by a reversion of the eye morphology to normal upon administration of the inhibitor. This method can include the condition where the insect is a fly, and where the fly is *Drosophila melanogaster*. The mutant eye morphology in the fly is rough eye. The candidate inhibitor can be a polynucleotide (for example a ribozyme or an antisense molecule), a polypeptide (for example, an intra-body or intracellular antibody), a small molecule, a peptide, or a peptoid.

Another embodiment of the invention is a transgenic fly containing a transgene comprising a polynucleotide of the invention under the regulatory control of an eye specific promoter, for example a sevenless or a GMR promoter, as described in Hay et al., *Development* 120:2121–9 (1994). The inhibitor is fed to the fly throughout the third instar larval development. Such a transgenic fly can be made from *Drosophila melanogaster*. The Drosophila is transformed with the transgene using standard techniques, and the transgenic fly is fed the inhibitor throughout the third instar larval development. Transgenic control flies and flies for which the inhibitors are ineffective exhibit a rough eye morphology as compared to a normal phenotype of the wild-type fly. An effective inhibitor reverts the rough eye phenotype to normal upon administration. The rough eye and other such aberrant morphology can be detected under a dissecting microscope as described in Kaufman et al., *Proc. Natl. Acad. Sci. USA* 92:10919–23 (1995). This assay has the advantage over in vitro assays in that inhibitors that revert the eye phenotype must also possess additional important properties required of a PI 3-kinase inhibiting pharmaceutical including that the inhibitor must be able to enter cells, that the inhibitor must be specific to the kinase target expressed as the transgene. The Drosophila eye screen can be used as a secondary or tertiary assay to test inhibitors that have been previously identified by other means.

The polynucleotides of the invention are useful as therapeutic agents in the context of trauma or potential cell death, for administration in a gene therapy vehicle for preventing the cell death that would result due to the trauma. The trauma can be, for example, a stroke or heart attack. Administration of such therapeutic agents is described below. The polynucleotides of the invention are also useful for treating type II diabetes in humans by administration of a gene therapy vehicle to human cells or tissue normally expected to produced an insulin-induced response but for the defectiveness of the cells or tissue to do so.

The inventors have observed that the expression of the polynucleotides of the invention markedly increases intracellular levels of $PI3,4P_2$ and $PI3,4,5P_3$. The level of phospholipid products induced correlates with the relative efficiencies of the activated p110-derived polynucleotides used. This observation supports the view that the 3' phosphorylated inositol phospholipid products mediate PI 3-kinase-induced signaling responses. However, as PI 3-kinase is a dual specificity kinase, that can phosphorylate phospholipids and proteins, a system to observe the phosphorylation of phospholipids in isolation was therefore devised.

Activation of the serine-threonine kinase Akt (also known as RAC-PK or PKB) has been shown to be dependent on PI 3-kinase, cotransfection of increasing amounts of Akt expression vectors with p110* results in increased levels of Akt activation, Akt contains a pleckstrin homology (PH) domain, and PH domains have been implicated in the binding of phospholipids and in the regulation of Akt activity, as described in Burgering et al., *Nature* 376: 599–602 (1995) and Harlan et al., *Nature* 371:168–70

(1994). By stimulation of intracellular protein kinase activity of Akt using purified p110*, it can be shown that this response is selectively mediated by the phosphatidylinositol product PI3,4P$_2$ and not by p110* protein kinase.

The assay comprises the steps of incubating a polynucleotide sequence of the invention with phosphatidylinositol 4 phosphate (PI4P) or phosphatidylinositol 4,5 bisph6sphate (PI4,5P$_2$,) to generate a 3' phosphorylated inositol phospholipid comprising phosphatidylinositol 3,4 bisphosphate (PI3, 4P$_2$,), or phosphatidylinositol 3,4,5 trisphosphate (PI3,4, 5P$_3$,), incubating the phosphatidylinositol 3,4,5 trisphosphate (PI3,4,5P$_3$,), with a signaling inositol polyphosphate 5' phosphatase (SIP) polypeptide, collecting phosphatidylinositol 3,4 bisphosphate (PI3,4P$_2$,), and contacting an active polypeptide having a pleckstrin homology domain with an effective amount of the phosphatidylinositol 3,4 bisphosphate (PI3,4P$_2$,). The enzyme effector of PI 3-kinase having a pleckstrin homology domain can be, for example, Akt kinase, one of several guanine nucleotide exchange factors, one of several GTPase activating proteins, and any other PH domain containing enzymes.

The use of inositol polyphosphate 5' phosphatase SIP (signaling inositol polyphosphate 5' phosphatase) converts the "inactive" (with respect to Akt activation) phospholipid product of PI 3-kinase, PI3,4,5P$_3$, into PI3,4P$_2$ that can stimulate Akt. Thus, the assay is useful to make PI3,4P$_2$, and to show that PI3,4P$_2$ is a specific membrane-bound product of PI 3-kinase (and perhaps also a product of SIP) that can directly activate PH domain-containing cytoplasmic signaling molecules. The protein SIP and nucleic acid encoding it is described in patent application Serial No. 08/624,190 filed Mar. 28, 1996.

By developing this assay, the inventors have developed a method of activating an enzyme effector of PI 3-kinase that has a pleckstrin homology domain, such as, Akt kinase, a guanine nucleotide exchange factor, GTPase activating proteins, or phospolipases. Also the method is a method of making the activating phospholipids. Once the phosphatidylinositol 3,4 bisphosphate (PI3,4P$_2$,). is made, a sufficient amount of it is placed in contact with an active kinase polypeptide having a pleckstrin homology domain, for example, Akt kinase, to test whether the synthesis is successful. Activation of Akt kinase is measured as described in the Example 6.

Using this method we determined that PI3,4P$_2$, but not PI3P or PI3,4,5P$_3$, increases Akt activity. We observed Akt activation by PI3,4P$_2$ using synthetic dipalmitoylated PI3, 4P$_2$ for in vitro stimulation of Akt, by generating PI3,4P$_2$-containing vesicles in vitro using p110* polynucleotide constructs and subsequently treating immobilized Akt, and by generating PI3,4P$_2$ by treating p110*-produced PI3,4,5P$_3$ with the inositol polyphosphate 5' phosphatase SIP in vitro. p110* did not appear to stimulate Akt by its protein kinase activity either in the presence or absence of phospholipid vesicles, because no Akt phosphorylation was detected in the presence of p110* despite the fact that p110* was able to autophosphorylate under the same reaction conditions. The possibility that the p110* protein kinase activity requires PI3,4P$_2$ to stimulate Akt does not seem likely, since Akt activation in vitro was also achieved using synthetic PI3,4P$_2$ in the absence of p110*. Thus, Akt is an immediate downstream effector of PI 3-kinase and the phosphatidylinositol products of PI 3-kinase can function as second messengers by directly activating Akt. This assay can be used to make and measure the production of intracellular 3' phosphorylated inositol phospholipids.

The assay allowed determination that the stimulatory effect of PI3,4P$_2$ on the kinase activity of Akt was dependent on the presence of a functional PH domain with the generation of a point mutation in the Akt PH domain that abrogated growth factor- or PI 3-kinase-mediated activation of Akt in vivo and that no longer allowed Akt stimulation by PI3,4P$_2$ in vitro. The discovery demonstrates that the PH domain is directly involved in the regulation of the enzymatic activity of Akt by PI3,4P$_2$. The experiments suggest that PI 3-kinase can activate signaling pathways through its 3' phosphorylated inositol phospholipid products that act on PH domains of effector molecules.

The phospholipids of the invention are useful as therapeutic agents also in the context of trauma or potential cell death, for reducing any potential cell death occurring from the trauma.

Administration

1. Gene Delivery Vehicles

Gene delivery vehicles (GDVs) are available for delivery of polynucleotides to cells, tissue, or to a the mammal for expression. For example, a polynucleotide sequence of the invention can be administered either locally or systemically in a GDV. These constructs can utilize viral or non-viral vector approaches in in vivo or ex vivo modality. Expression of such coding sequence can be induced using endogenous mammalian or heterologous promoters. Expression of the coding sequence in vivo can be either constitutive or regulated.

The invention includes gene delivery vehicles capable of expressing the contemplated polynucleotides. The gene delivery vehicle is preferably a viral vector and, more preferably, a retroviral, adenoviral, adeno-associated viral (AAV), herpes viral, or alphavirus vectors. The viral vector can also be an astrovirus, coronavirus, orthomyxovirus, papovavirus, paramyxovirus, parvovirus, picornavirus, poxvirus,-togavirus viral vector. See generally, Jolly, *Cancer Gene Therapy* 1:51–64 (1994); Kimura, *Human Gene Therapy* 5:845–852 (1994), Connelly, *Human Gene Therapy* 6:185–193 (1995), and Kaplitt, *Nature Genetics* 6:148–153 (1994).

Retroviral vectors are well known in the art and we contemplate that any retroviral gene therapy vector is employable in the invention, including B, C and D type retroviruses, xenotropic retroviruses (for example, NZB-X1, NZB-X2 and NZB9-1 (see O'Neill, *J. Vir.* 53:160, 1985) polytropic retroviruses (for example, MCF and MCF-MLV (see Kelly, *J. Vir.* 45:291, 1983), spumaviruses and lentiviruses. See RNA Tumor Viruses, Second Edition, Cold Spring Harbor Laboratory, 1985.

Portions of the retroviral gene therapy vector may be derived from different retroviruses. For example, retrovector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

These recombinant retroviral vectors may be used to generate transduction competent retroviral vector particles by introducing them into appropriate packaging cell lines (see U.S. Ser. No. 07/800,921, filed Nov. 29, 1991). Retrovirus vectors can be constructed for site-specific integration into host cell DNA by incorporation of a chimeric integrase enzyme into the retroviral particle. See, U.S. Ser. No. 08/445,466 filed May 22, 1995. It is preferable that the recombinant viral vector is a replication defective recombinant virus.

Packaging cell lines suitable for use with the above-described retrovirus vectors are well known in the art, are readily prepared (see U.S. Ser. No. 08/240,030, filed May 9, 1994; see also WO 92/05266), and can be used to create producer cell lines (also termed vector cell lines or "VCLs") for the production of recombinant vector particles. Preferably, the packaging cell lines are made from human parent cells (e.g., HT1080 cells) or mink parent cell lines, which eliminates inactivation in human serum.

Preferred retroviruses for the construction of retroviral gene therapy vectors include Avian Leukosis Virus, Bovine Leukemia, Virus, Murine Leukemia Virus, Mink-Cell Focus-Inducing Virus, Murine Sarcoma Virus, Reticuloendotheliosis Virus and Rous Sarcoma Virus. Particularly preferred Murine Leukermia Viruses include 4070A and 1504A (Hartley and Rowe, *J. Virol.* 19:19–25, 1976), Abelson (ATCC No. VR-999), Friend (ATCC No. VR-245), Graffi, Gross (ATCC No. VR-590), Kirsten, Harvey Sarcoma Virus and Rauscher (ATCC No. VR-998) and Moloney Murine Leukemia Virus (ATCC No. VR-190). Such retroviruses may be obtained from depositories or collections such as the American Type Culture Collection ("ATCC") in Rockville, Md. or isolated from known sources using commonly available techniques.

Exemplary known retroviral gene therapy vectors employable in this invention include those described in GB 2200651; EP No. 415,731; EP No. 345,242; PCT Publication Nos. WO 89/02468, WO 89/05349, WO 89/09271, WO 90/02806, WO 90/07936, WO 90/07936, WO 94/03622, WO 93/25698, WO 93/25234, WO 93/11230, WO 93/10218, and WO 91/02805, in U.S. Pat. Nos. 5,219,740, 4,405,712, 4,861,719, 4,980,289 and 4,777,127, in U.S. Ser. No. 07/800,921 and in Vile, *Cancer Res.* 53:3860–3864 (1993); Vile, *Cancer Res* 53:962–967 (1993); Ram, *Cancer Res* 53:83–88 (1993); Takamiya, *J. Neurosci. Res.* 33:493–503 (1992); Baba, *J Neurosurg* 79:729–735 (1993); Mann, *Cell* 33:153 (1983); Cane, *Proc Natl Acad Sci* 81:6349 (1984) and Miller, *Human Gene Therapy* 1 (1990).

Human adenoviral gene therapy vectors are also known in the art and employable in this invention. See, for example, Berkner, *Biotechniques* 6:616 (1988), and Rosenfeld, *Science* 252:431 (1991), and PCT Patent Publication Nos. WO 93/07283, WO 93/06223, and WO 93/07282. Exemplary known adenoviral gene therapy vectors employable in this invention include those described in the above-referenced documents and in PCT Patent Publication Nos. WO 94/12649, WO 93/03769, WO 93/19191, WO 94/28938, WO 95/11984, WO 95/00655, WO 95/27071, WO 95/29993, WO 95/34671, WO 96/05320, WO 94/08026, WO 94/11506, WO 93/06223, WO 94/24299, WO 95/14102, WO 95/24297, WO 95/02697, WO 94/28152, WO 94/24299, WO 95/09241, WO 95/25807, WO 95/05835, WO 94/18922 and WO 95/09654. Alternatively, administration of DNA linked to killed adenovirus as described in Curiel, *Hum. Gene Ther.* 3:147–154 (1992) may be employed.

The gene delivery vehicles of the invention also include adenovirus associated virus (AAV) vectors. Leading and preferred examples of such vectors for use in this invention are the AAV-2 basal vectors disclosed in Srivastava, PCT Patent Publication No. WO 93/09239. Most preferred AAV vectors comprise the two AAV inverted terminal repeats in which the native D-sequences are modified by substitution of nucleotides, such that at least 5 native nucleotides and up to 18 native nucleotides, preferably at least 10 native nucleotides up to 18 native nucleotides, most preferably 10 native nucleotides are retained and the remaining nucleotides of the D-sequence are deleted or replaced with non-native nucleotides. The native D-sequences of the AAV inverted terminal repeats are sequences of 20 consecutive nucleotides in each AAV inverted terminal repeat (i.e., there is one sequence at each end) which are not involved in HP formation. The non-native replacement nucleotide may be any nucleotide other than the nucleotide found in the native D-sequence in the same position. Other employable exemplary AAV vectors are pWP-19, pWN-1, both of which are disclosed in Nahreini, *Gene* 124:257–262 (1993). Another example of such an AAV vector is psub201. See Samulski, *J. Virol.* 61:3096 (1987). Another exemplary AAV vector is the Double-D ITR vector. How to make the Double D ITR vector is disclosed in U.S. Pat. No. 5,478,745. Still other vectors are those disclosed in Carter, U.S. Pat. No. 4,797,368 and Muzyczka, U.S. Pat. No. 5,139,941, Chartejee, U.S. Pat. No. 5,474,935, and Kotin, PCT Patent Publication No. WO 94/288157. Yet a further example of an AAV vector employable in this invention is SSV9AFABTKneo, which contains the AFP enhance and albumin promoter and directs expression predominantly in the liver. Its structure and how to make it are disclosed in Su, *Human Gene Therapy* 7:463–470 (1996). Additional AAV gene therapy vectors are described in U.S. Pat. Nos. 5,354,678; 5,173,414; 5,139, 941; and 5,252,479.

The gene therapy vectors of the invention also include herpes vectors. Leading and preferred examples are herpes simplex virus vectors containing a sequence encoding a thymidine kinase polypeptide such as those disclosed in U.S. Pat. No. 5,288,641 and EP No. 176,170 (Roizman). Additional exemplary herpes simplex virus vectors include HFEM/ICP6-LacZ disclosed in PCT Patent No. WO 95/04139 (Wistar Institute), pHSVlac described in Geller, *Science* 241:1667–1669 (1988) and in PCT Patent Publication Nos. WO 90/09441 and WO 92/07945, HSV Us3::pgC-lacZ described in Fink, *Human Gene Therapy* 3:11–19 (1992) and HSV 7134, 2 RH 105 and GAL4 described in EP No. 453,242 (Breakefield), and those deposited with the ATCC as accession numbers ATCC VR-977 and ATCC VR-260.

Alpha virus gene therapy vectors may be employed in this invention. Preferred alpha virus vectors are Sindbis viruses vectors. Togaviruses, Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described U.S. Pat. Nos. 5,091,309 and 5,217,879, and PCT Patent Publication No. WO 92/10578. More particularly, those alpha virus vectors described in U.S. Ser. No. 08/405,627, filed Mar. 15, 1995, and U.S. Ser. No. 08/198,450 and in PCT Patent Publication Nos. WO 94/21792, WO 92/10578, and WO 95/07994, and U.S. Pat. Nos. 5,091,309 and 5,217,879 are employable. Such alpha viruses may be obtained from depositories or collections such as the ATCC in Rockville, Md. or isolated from known sources using commonly available techniques. Preferably, alphavirus vectors with reduced cytotoxicity are used (see co-owned U.S. Ser. No. 08/679640).

DNA vector systems such as eukaryotic layered expression systems are also useful for expressing the nucleic acids of the invention. See PCT Patent Publication No. WO 95/07994 for a detailed description of eukaryotic layered expression systems. Preferably, the eukaryotic layered expression systems of the invention are derived from alphavirus vectors and most preferably from Sindbis viral vectors.

Other viral vectors suitable for use in the present invention include those derived from poliovirus, for example ATCC VR-58 and those described in Evans, *Nature* 339:385

(1989), and Sabin, *J. Biol. Standardization* 1:115 (1973); rhinovirus, for example ATCC VR-1110 and those described in Arnold, *J Cell Biochem* (1990) L40 1; pox viruses such as canary pox virus or vaccinia virus, for example ATCC VR-111 and ATCC VR-2010 and those described in Fisher-Hoch, *Proc Natl Acad Sci* 86 (1989) 317, Flexner, *Ann NY Acad Sci* 569:86 (1989), Flexner, *Vaccine* 8:17 (1990); in U.S. Pat. Nos. 4,603,112 and 4,769,330 and in WO 89/01973; SV40 virus, for example ATCC VR-305 and those described in Mulligan, *Nature* 277:108 (1979) and Madzak, *J Gen Vir* 73:1533 (1992); influenza virus, for example ATCC VR-797 and recombinant influenza viruses made employing reverse genetics techniques as described in U.S. Pat. No. 5,166,057 and in Enami, *Proc. Natl. Acad. Sci.* 87:3802–3805 (1990); Enami and Palese, *J. ViroL* 65:2711–2713 (1991); and Luytjes, *Cell* 59:110 (1989), (see also McMicheal., *New England J. Med.* 309:13 (1983), and Yap, *Nature* 273:238 (1978) and *Nature* 277:108, 1979); human immunodeficiency virus as described in EP No. 386,882 and in Buchschacher, *J. Vir.* 66:2731(1992); measles virus, for example, ATCC VR-67 and VR-1247 and those described in EP No. 440,219; Aura virus, for example, ATCC VR-368; Bebaru virus, for example, ATCC VR-600 and ATCC VR-1240; Cabassou virus, for example, ATCC VR-922; Chikungunya virus, for example, ATCC VR-64 and ATCC VR-1241; Fort Morgan Virus, for example, ATCC VR-924; Getah virus, for example, ATCC VR-369 and ATCC VR-1243; Kyzylagach virus, for example, ATCC VR-927; Mayaro virus, for example, ATCC VR-66; Mucambo virus, for example, ATCC VR-580 and ATCC VR-1244; Ndumu virus, for example, ATCC VR-371; Pixuna virus, for example, ATCC VR-372 and ATCC VR-1245; Tonate virus, for example, ATCC VR-925; Triniti virus, for example ATCC VR-469; Una virus, for example, ATCC VR-374; Whataroa virus, for example ATCC VR-926; Y-62–33 virus, for example, ATCC VR-375; O'Nyong virus, Eastern encephalitis virus, for example, ATCC VR-65 and ATCC VR-1242; Western encephalitis virus, for example, ATCC VR-70, ATCC VR-1251, ATCC VR-622 and ATCC VR-1252; and coronavirus, for example, ATCC VR-740 and those described in Hamre, *Proc. Soc. Exp. Biol. Med.* 121:190 (1966).

Delivery of the compositions of this invention into cells is not limited to the above mentioned viral vectors. Other delivery methods and media may be employed such as, for example, nucleic acid expression vectors, polycationic condensed DNA linked or unlinked to killed adenovirus alone, for example see U.S. Ser. No. 08/366,787, filed Dec. 30, 1994, and Curiel, *Hum Gene Ther* 3:147–154 (1992) ligand linked DNA, for example, see Wu, *J. Biol. Chem.* 264:16985–16987 (1989), eucaryotic cell delivery vehicles cells, for example see U.S. Ser. No. 08/240,030, filed May 9, 1994, and U.S. Ser. No. 08/404,796, deposition of photopolymerized hydrogel materials, hand-held gene transfer particle gun, as described in U.S. Pat. No. 5,149,655, ionizing radiation as described in U.S. Pat. No. 5,206,152 and in PCT Patent Publication No. WO 92/11033, nucleic charge neutralization or fusion with cell membranes. Additional approaches are described in Philip, *Mol. Cell. Biol.* 14:2411–2418 (1994) and in Woffendin, *Proc. Natl. Acad. Sci.* 91:1581–585 (1994).

Particle mediated gene transfer may be employed, for example see U.S. provisional application No. 60/023,867. Briefly, the sequence can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, as described in Wu and Wu, *J. Biol. Chem.* 262:4429–4432 (1987), insulin as described in Hucked, *Biochem. Pharmacol.* 40:253–263 (1990), galactose as described in Plank, *Bioconjugate Chem* 3:533–539 (1992), lactose or transferrin.

Naked DNA may also be employed. Exemplary naked DNA introduction methods are described in PCT Patent Publication No. WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm.

Liposomes that can act as gene delivery vehicles are described in U.S. Pat. No. 5,422,120, PCT Patent Publication Nos. WO 95/13796, WO 94/23697, and WO 91/144445, and EP No. 524,968. As described in co-owned U.S. provisional application No. 60/023,867, on non-viral delivery, the nucleic acid sequences can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquitously-active promoters. Further non-viral delivery suitable for use includes mechanical delivery systems such as the approach described in Woffendin et al., *Proc. Natl. Acad. Sci. USA* 91(24):11581–11585 (1994). Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT Patent Publication No. WO 92/11033.

Exemplary liposome and polycationic gene delivery vehicles are those described in U.S. Pat. Nos. 5,422,120 and 4,762,915, in PCT Patent Publication Nos. WO 95/13796, WO 94/23697, and WO 91/14445, in EP No. 524,968 and in Stryer, *Biochemistry*, pages 236–240 (1975) W. H. Freeman, San Francisco, Szoka, *Biochem. Biophys. Acta.* 600:1 (1980); Bayer, *Biochem. Biophys. Acta.* 550:464 (1979); Rivnay, *Meth. Enzymol.* 149:119 (1987); Wang, *Proc. Natl. Acad. Sci.* 84:7851 (1987); and Plant, *Anal. Biochem.* 176:420 (1989).

Administration of the Phospholipids

The phospholipids of the invention can be used to treat cell death in humans or other mammalian patients by contacting the a pharmaceutical composition containing the phospholipids with a cell that has experienced trauma, for example a trauma from a heart attack or a stroke.

In a therapeutic context, the phospholipids of the invention can be administered as described in Franke et al, *Science* 275:665–668 (1997), for example by placing the phospholipid containing vesicles in contact with cells in which they can be internalized. Therefore administration of the phospholipids of the invention include all the local and systemic modes of administration possible.

Pharmaceutical Compositions and Therapeutic Methods

The gene delivery vehicles containing the polynucleotides or phospholipids of the invention can be administered, locally or systemically to mammals; especially humans or primates, or placed in direct contact with a cell or population of cells. The phospholipids and gene therapy vectors can be formulated into pharmaceutical compositions as described below. The pharmaceutical compositions comprise gene therapy vectors containing a polynucleotide of the invention or a phospholipid made by the method of the invention in a pharmaceutically acceptable carrier or diluent.

Suitable carriers may be large, slowly metabolized macromolecules such as proteins, polysaccharides, polylactic acids, polyglycolic acids, polymeric amino acids, amino acid copolymers, and inactive viruses in particles. Such carriers are well known to those of ordinary skill in the art. Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in REMINGTON'S PHARMACEUTICAL SCIENCES (Mack Pub. Co., N.J. 1991). Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

A "therapeutically effective amount" is that amount of any of the pharmaceutical compositions that are administered will be that amount sufficient to generate the desired therapeutic outcome.

The term "pharmaceutically acceptable carrier" refers to a carrier for administration of a therapeutic agent that does not itself induce the production of antibodies harmful to the individual receiving the composition, and which may be administered without undue toxicity. Pharmaceutical compositions can include a recombinant viral vector as described above, in combination with a pharmaceutically acceptable carrier or diluent. Such pharmaceutical compositions may be prepared either as a liquid solution, or as a solid form (e.g., lyophilized) which is suspended in a solution prior to administration. In addition, the composition may be prepared with suitable carriers or diluents for either surface administration, injection, oral, or rectal administration. Pharmaceutically acceptable carriers or diluents are nontoxic to recipients at the dosages and concentrations employed. Representative examples of carriers or diluents for injectable solutions include water, isotonic saline solutions which are preferably buffered at a physiological pH (such as phosphate-buffered saline or Tris-buffered saline), mannitol, dextrose, glycerol, and ethanol, as well as polypeptides or proteins such as human serum albumin. A particularly preferred composition comprises a vector or recombinant virus in 10 mg/ml mannitol, 1 mg/ml HSA, 20 mM Tris, pH 7.2, and 150 mM NaCl. In this case, since the recombinant vector represents approximately 1 mg of material, it may be less than 1% of high molecular weight material, and less than 1/100,000 of the total material (including water). This composition is stable at −70|C for at least six months.

Pharmaceutical compositions of the present invention may also additionally include factors that stimulate cell division, and hence, uptake and incorporation of a recombinant retroviral vector. Preserving recombinant viruses is described in US applications entitled "Methods for Preserving Recombinant Viruses" (U.S. Ser. No. 08/135,938, filed Oct. 12, 1993) which is incorporated herein by reference in full.

The pharmaceutically acceptable carrier or diluent may be combined with the gene delivery vehicles of with the phospholipids to provide a composition either as a liquid solution, or as a solid form (e.g., lyophilized) which can be resuspended in a solution prior to administration. The two or more gene delivery vehicles are typically administered via traditional direct routes, such as buccal/sublingual, rectal, oral, nasal, topical, (such as transdermal and ophthalmic), vaginal, pulmonary, intraarterial, intramuscular, intraperitoneal, subcutaneous, intraocular, intranasal or intravenous, or indirectly.

Any therapeutic of the invention, including, for example, polynucleotides for expression in the mammal or phospholipids, can be formulated into an enteric coated tablet or gel capsule according to known methods in the art. These are described in the following patents: U.S. Pat. No. 4,853,230, EP No. 225,189, AU 9,224,296, AU 9,230,801, and WO 92144,52. Such a capsule is administered orally to be targeted to the jejunum. At 1 to 4 days following oral administration expression of the polypeptide, or inhibition of expression by, for example a ribozyme or an antisense oligonucleotide, is measured in the plasma and blood, for example by antibodies to the expressed or non-expressed proteins.

Administration can be accomplished by any means appropriate for the therapeutic agent, for example, by parenteral or oral delivery. The parenteral delivery can be subcutaneous, intravenous, intramuscular, intra-arterial, injection into the tissue of an organ, mucosal, pulmonary, topical, or catheter-based. Oral means is by mouth, including pills or other gastroenteric delivery means, including a drinkable liquid. Mucosal delivery can include, for example, intranasal delivery. Pulmonary delivery can include inhalation of the agent. Catheter-based delivery can include delivery by iontophoretic catheter-based delivery. Administration will generally also include delivery with a pharmaceutically acceptable carrier, such as a buffer, a polypeptide, a peptide, a polysaccharide conjugate, a liposome, and a lipid. A gene therapy protocol is considered an administration in which the therapeutic agent is a polynucleotide capable of accomplishing a therapeutic goal when expressed as a transcript or a polypeptide in the mammal, and can be applied to both parenteral and oral delivery means. Such administration means will be selected as appropriate for the disease being treated. For example, where the disease is organ-based, delivery may be local, and for example, where the disease is systemic, the delivery may be systemic.

The term "in vivo administration" refers to administration to a patient, for example a mammal, of a polynucleotide encoding a polypeptide for expression in the mammal. In particular, direct in vivo administration involves transfecting a mammal's cell with a coding sequence without removing the cell from the mammal. Thus, direct in vivo administration may include direct injection of the DNA encoding the polypeptide of interest in the region afflicted by trauma, or to the region where glucose uptake is regulated.

The term "ex vivo administration" refers to transfecting a cell, for example, a cell from a population of cells that are deficient in their normal function of glucose-uptake, after the cell is removed from the patient. After transfection the cell is then replaced in the patient. Ex vivo administration can be accomplished by removing cells, transforming them with a polynucleotide of the invention, including also a regulatory region for facilitating the expression, and placing the transformed cells back into the patient for expression.

The gene delivery vehicle or phospholipid can be introduced into a population of cells or a mammal, for example, by injection, particle gun, topical administration, parental administration, inhalation, or iontophoretic delivery, as described in U.S. Pat. Nos. 4,411,648; 5,222,936; and 5,286,254; and PCT Patent Publication No. WO 94/05369.

The gene delivery vehicle may be administered at single or multiple sites to a mammal directly, for example by direct injection, or alternatively, through the use of target cells transduced ex vivo. The present invention also provides pharmaceutical compositions (including, for example, various exipients) suitable for administering the gene delivery vehicles. Within the context of the present invention, it should be understood that the removed cells may be returned to the same animal, or to another allogenic animal or mammal. In such a case it is generally preferable to have histocompatibility matched animals (although not always, see, e.g., Yamamoto et al., "Efficacy of Experimental FIV Vaccines," 1st International Conference of FIV Researchers, University of California at Davis, September, 1991.

The multiple gene delivery vehicles or phospholipids may be administered to animals, plants, or to a population of cells. In preferred embodiments, the animal is a warm-blooded animal, further preferably selected from the group consisting of mice, chickens, cattle, pigs, pets such as cats and dogs, horses, and humans.

For polynucleotide therapeutics, depending on the expression of the polynucleotide in the target cell, vectors containing expressable constructs of coding sequences, or non-coding sequences can be administered in a range of about 100 ng to about 200 mg of DNA for local administration in a gene therapy protocol, also about 500 ng to about 50 mg, also about 1 ug to about 2 mg of DNA, about 5 ug of DNA to about 500 ug of DNA, and about 20 ug to about 100 ug during a local administration in a gene therapy protocol, and for example, a dosage of about 500 ug, per injection or administration. Where greater expression is desired, over a larger area of tissue, larger amounts of DNA or the same amounts readministered in a successive protocol of administrations, or several administrations to different adjacent or close tissue portions of for example, a tumor site, may be required to effect a positive therapeutic outcome.

Phospholipid therapeutic agents can be administered in dosage effective for the amount of cells targeted, in such quantities as analogously appropriate to the amounts of phospholipids effective as described in Franke et al., *Science* 275:665–668 (1997).

Administration of a gene delivery vehicle having a polynucleotide of the invention for preventing or reducing cell death, or administration of a 3' phosphorylated phospholipid, or a vesicle containing such, for the purpose of preventing or reducing cell death, can be made directly to a putative site of trauma, or can be made systemically, but the vehicle or vesicle can be targeted specifically to the putative site of trauma. Administration of a polynucleotide of the invention can also be made directly to cells exhibiting insulin resistance, such as for example liver cells, or other cells expected under normal conditions to be responsive to insulin.

In all cases, routine experimentation in clinical trials will determine specific ranges for optimal therapeutic effect, for each therapeutic, each administrative protocol, and administration to specific mammals will also be adjusted to within effective and safe ranges depending on the mammal condition and responsiveness to initial administrations.

Further objects, features, and advantages of the present invention will become apparent from the detailed description. It should be understood, however, that the detailed description, while indicating preferred embodiments of the invention, is given by way of illustration only, since various changes and modifications within the spirit and scope of the invention will become apparent to those skilled in the art from this detailed description. Also, the invention is not limited by any theories of mechanism of the method of the invention.

EXAMPLE 1

Construction of Growth Factor Independent Membrane Targeted PI 3-Kinase Mutants

Growth factor independent membrane targeted p110 derived PI 3-kinase mutants were constructed by the addition of heterologous membrane targeting signals to the polynucleotide sequences encoding either a p110 subunit, p110* or any other p110 derived variant of PI 3-kinase. p110* can be constructed, for example, as described in Hu et al, *Science* 268: 100–102 (1995), and consists of the basic functional elements of the PI 3-kinase subunits, providing for the iSH2 domain of p85 attached to a p110 subunit.

As depicted schematically in FIG. 1, p110 constructions were tagged either at the N- or C-terminal end with the Myc epitope depicted by the oval. The iSH2 fragment of p85 contained a C-terminal influenza virus hemagglutinin (HA) epitope tag depicted by the diamond. The p110 region with. homology to the catalytic domain of protein kinases is depicted by a box labeled "kinase". The domain responsible for the interaction with the iSH2 domain of the p85 subunit is shown as a small box at the p110 N-terminus. p110Δkin is a kinase-deficient p110, in which the arginine at position 802 was mutated to a lysine residue as indicated by an asterik within the catalytic domain. The iSH2 domain of p85 that is required for catalytic activity is represented by a hatched bar. The first and last amino acids of fragments are numbered with respect to their position in the wt p85 or p110 sequence. p110* is a constitutively active chimera that contains the iSH2 domain of p85 attached to the N-terminus of p110 via a flexible "glycine linker" as described in Hu et al., *Science* 268:100–102 (1995). The p110*Δkin is the kinase-deficient version of p110*. Myr-P110 and Myr-P110* as well as their kinase deficient versions were modified at their respective N-terminal ends with the myristoylation sequence of pp60 c-Src as described in Kaplan et al., *PNAS USA* 83: 3624–8 (1990), Schultz et al., *Science* 227:427–9 (1985), and Deichaite et al, *Mol. Cell Biol* 8:4295–301 (1988). The C-terminal ends of p110-H and p110*-H and their kinase-deficient versions were extended by the farnesylation and palmitoylation sequences of H-Ras, as described by Cadwallader et al., *Mol. Cell Biol.* 14:4722–30 (1994). Similarly, polynucleotide sequences containing the farnesylation sequence and polybasic stretch of K-Ras were generated as described in Cadwallader et al., *Mol. Cell Biol.* 14:4722–30 (1994).

The p110 and p110* variants that were constructed for this example were, M-p110 and M-p110* which contains the N-terminal myristoylation sequence of phosphoprotein 60

(pp60) c-Src and a C-terminal Myc epitope tag, p110-H and p110-K, and p110*-H and p110*-K that carry an N-terminal Myc epitope-tag. pp110-H and p110*-H have a C-terminal farnesylation and palmitoylation signal which sequences are derived from H-Ras, and p110-K and p110*-K have a C terminal farnesylation signal and a polybasic sequence, which sequences are derived from K-Ras. These variants were constructed by N-terminus and C-terminus modifications of polynucleotides encoding polypeptides of p110* and p110. The p110* or p110 mutants were modified at the N-terminus by the pp60 c-Src myristoylation sequence as described in Kaplan et al., *Mol. Cell. Biol.* 10: 1000–9 (1990), Schultz, et al., *Science* 227:427–9 (1985), and Deichaite et al., *Mol. Cell. Biol.* 8:4295–301 (1988), using primers Src-M-sense (5'C ATG GGG AGC AGC AAG AGC AAG CCC AAG GAC CCC AGC CAG CGC GGGGGGA CA 3) SEQ ID NO. 12, and SrcM antisense (5'TAT GTC CCC CGC GCT GGC TGG GGT CCT TGG TCG TCT TGC TGC TCC C 3') SEQ ID NO. 11 flanked by NcoI and NdeI restriction sites where A at position 2 is the cSrc start codon. The annealed DNA fragment was attached in frame via the respective restriction sites to the N-terminus of a Myc-tagged p110 cDNA constructed as described in Klippel et al., *Mol. Cell. Biol.* 14:2675–2685 (1994) into a mammalian expression vector that directs expression from the SRα promoter as described in Takabe et al., *Mol. Cell Biol.* 8:466–72 (1988).

To modify the C-terminal end of any p110 subunit derived mutant with the H-Ras farnesylation and palmitoylation signals or the K-Ras farnesylation signals and polybasic sequences, as described in Cadwallader et al., *Mol. Cell. Biol.* 14:4722–30 (1994), a C-terminal fragment of the p110 cDNA was amplified using primer p110—3' HindIII (5° CTG AGC AAG AAG CTT TGG 3'), SEQ ID NO. 10, consisting of nucleotides 3092 to 3109 of the coding strand overlapping a HindIII site, and a primer p110-H (5' GGA TCC TCA GCT CAG CAC GCA CTT GCA GCT CAT GCA GCC GGG GCC GCT GCT GGC GCC CCC GAG CTC GTT CAA AGC ATG CTG 3') SEQ ID NO. 9 where the underlined portion indicates nucleotides that are changed with respect to the wild-type sequence, overlapping nucleotides 3109 to 3204 of the noncoding strand, where A of the start codon is designated nucleotide 1. This extended the p110 C-terminal end by a sequence encoding amino-acids DLGGA (SEQ ID No. 3) as a hinge region containing overlapping restriction site for SacI and Ecl136II, and KasI and NarI, which precedes the coding region for the H-Ras CAAX box, a stop-codon, and a BamHI restriction site. The C-terminal end of p110 was modified with K-Ras farnesylation sequence plus a polybasic region as described in Cadwallader et al, *Mol. Cell. Biol.* 14: 4722–30 (1994), by PCR using primer p110 3' HindIII and primer p110-K (5' GCA TTC TCA CAT GAT CAC GCA CTT GGT CTT GGA CTT CTT CTT CTT CTT TTT GCC ATC TTT GGA GGC GCC GAG CTC GTT CAA AGC ATC CTG 3'), SEQ ID NO. 8. This extended the p110 C-terminal end by a sequence encoding amino-acids DLGGA (SEQ ID No. 3) as a hinge region containing overlapping restriction sites for Sacd and Ecl136II, and KasI and NarI, which precedes the coding region for the K-Ras farnesylation and polylysine sequence, a stop-codon, and a BamHI restriction site. The Myc-tagged C-terminal end of p110, constructed as described in Klippel et al., *Mol. Cell. Biol.* 14:2675–2685 (1994) was exchanged against the H-Ras or K-Ras CAAX-box modified sequences using HindIII and BamHI. For the C-terminal farnesylated p110 constructs, the N-terminal end of the p110 coding region was modified with the 10-amino acid Myc epitope consisting of EQKLISEEDL, SEQ ID NO. 7, as described in Evan et al., *Mol. Cell Biol.* 5:3610–6 (1985), using primer p110 5'-Myc sense (5'CT AGA ATG GAT GAG CAG AAG CTG ATT TCC GAG GAG GAC CTG AAC GGG GGA CA 3') SEQ ID NO. 6, and primer p110 5' Myc—antisense (5'T ATG TCC CCC GTT CAG GTCCTC CTC GGA AAT CAG CTT CTG CTC ATC CAT T 3'), SEQ ID NO. 5, flanked by restriction sites for XbaI and NdeI. The Myc-coding region was attached in frame to the wild-type p110 N-terminus by ligating the annealed oligonucleotide via XbaI-NdeI ends into pCG-P 110 as described in Klippel et al., *Mol. Cell. Biol.* 14:2675–2685 (1994).

Kinase deficient control mutants, called generically p110ΔKin, were constructed by changing a lysine at position 802 to an arginine residue, which alteration was accomplished by site-directed mutagenesis using the gapped duplex DNA method as described in Stanssens et al, *Nuc. Acids Res.* 17:4441–54 (1989) with primer p110-KR802 (5'C GTC GCC ATT TCT AAA GAT GAT CTC 3'), SEQ ID NO. 4, where the underlined C indicates the point of mutation, and annealing to nucleotides 2392 to 3016 of the p110 coding region. The correct sequence of the p110 fragments modified by PCR or oligonucleotides was confirmed by DNA sequence analysis.

The N-terminal myristoylation or C-terminal H-Ras farnesylation or K-Ras palmitoylation sequences were furthermore used to modify the coding regions for p110Δkin, p110*, and p110*Δkin by using restriction described above for p110. For expression of p110 molecules in COS-7 cells, the respective DNA fragments were cloned into mammalian expression vector pCG via XbaI-BamHI ends as described in Klippel et al., *Mol. Cell. Biol.* 14: 2675–2685 (1994). Plasmid pCG is a derivative of vectors described by Matthias et al, *Nuc. Acids Res.* 17:6418 (1989), and directs expression in mammalian cells from the human cytomegalovirus promoter/enhancer region. COS-7 cells were obtained from the American Type Culture Collection and cultured at 37° C. in Dulbecco's modified Eagle medium containing 10% bovine calf serum, and penicillin at a concentration of 50 μg/ml and streptomycin at a concentration of 50 μg/ml.

EXAMPLE 2

Transient Expression of Recombinant p110 Derivatives in COS Cells and the Intracellular Distribution of p110 Molecules After Expression COS-7 cells that were 60% to 70% confluent on a 10 cm plate were transfected with mammalian expression vectors using the DEAE-dextran method as described in Gorman, Glover ed. DNA Cloning: A Practical Approach, v.II, IRL Press, Oxford, p.143–190 (1985). The cells were starved for at least 30 hours in medium containing 0.5% dialyzed fetal bovine calf serum and then treated with or without platelet-derived growth factor hormone (PDGF) at a concentration of 2 nM for 10 minutes at 37° C. The COS07 cells were washed twice with cold phosphate-buffered saline and lysed at 4° C. in a mammalian cell lysis buffer containing the following: 20 mM Tris at pH 7.5, 137 mM NaCl, 15% v/v glycerol, 1% v/v Triton X-100, 2 mM EDTA, 2 mM phenylmethylsulfonyl fluoride, 10 mg aprotinin per ml, 20 mM leupeptin, 2 mM benzamide, 1 mM sodium vanadate, 25 mM β-glycerolphosphate, 50 mM NaF and 10 mM NaPpi. The lysates were cleared by centrifugation at 14,000×g for 5 minutes and aliquots of the lysates were analyzed for protein expression and enzyme activity.

To investigate the intracellular distribution of p110 molecules, hypotonic lysates were prepared as described in Cadwallader et al., *Mol. Cell. Biol.* 14:4722–30 (1994), including that COS-7 cells were scraped in ice-cold PBS into microfuge tubes and collected at 400×g for 2 minutes. The cells were lysed by Dounce homogenization on ice in 500 µl of 10 mM N-2-hydroxyethylpiperazine-N'-2-ethanesulfonic acid (Hepes) pH 7.5, 10 mM Kcl, 1.5 $MgCl_2$, 0.3 mM ethylene glycol-bis (β-aniinoethyl ether)-N, N, N', N'-tetraacetic acid (EGTA), 2 mM phenylmethylsulfonyl fluoride, 10 mg aprotinin per ml, 20 mM leupeptin, 2 mM benzamidine, 1 mM sodium vanadate, 25 mM β-glycerolphosphate, 50 mM NaF and 10 mM NaPPi for 10 minutes. After removal of the nuclei and unbroken cells at centrifugation at 1,500×g for 5 minutes, the membranes were pelleted for 30 minutes at 120,000×g in a TLA 120.2 rotor made by Beckman Instruments, Palo Alto, Calif. The supernatant called S100 and the pellet called P100 fractions were collected and equal proportions were analyzed for protein distribution by immunoblotting with antibodies specific for the tagged proteins.

Immunoblotting for purposes of determining the protein distribution was performed by boiling inimunoprecipitates in Lammli-sarnple buffer, separating the immunoprecipitates from the unprecipitated proteins by SDS-PAGE and by transferring the immunoprecipitates to nitrocellulose filters. The filters were blocked in TBST buffer composed of 10 mM Tris-HCl (pH 7.5), 150 mM NaCl, 0.5% v/v Tween 20, and 0.5% w/v sodium azide containing 5% w/v dried milk. The respective antibodies were added in TBST at appropriate dilutions. Bound antibody was detected with anti-mouse or anti-rabbit conjugated to alkaline phosphatase made by Promega Corporation, Madison, Wis., in TBST, washed, and developed with nitroblue tetrazolium and 5-bromo-4-chloro-3-indolyl phosphate also by Promega. Alternatively, horseradish peroxidase conjugated anti-mouse antibody was used and developed by enhanced chemiluminescence made by Amersham Life *Sciences, located at Arlington Heights, Ill.*

EXAMPLE 3

In Vitro Protein Kinase Assays and Determination of PI 3-kinase Activity in p110 Precipitates Cell lysates containing HA-tagged pp70 S6 kinase, Akt-kinase, MAP-kinase or cJun terminal kinase (JNK) were incubated with monoclonal anti-HA antibody 12CA5 for 1 hour at 4° C. Protein A-Sepharose beads (Sigma, St. Louis, Mo.) were used to precipitate the immune complexes. The beads were washed with 50 mM Tris-HCl (pH 7.5), 0.5 M LiCl, 0.5% v/v Triton X-100, twice with PBS and once with 10 mM Tris-HCl (pH 7.5), 10 mM $MgCl_2$, 1 mM dithiothreitol, all containing 0.1 mM sodium vanadate and 20 mM β-glycerolphosphate. For analyzing the immune complexes in an S6 kinase activity assay the beads were divided in three aliquots: two aliquots were subjected to a S6 kinase activity assay using [$\lambda$-$^{32}$p] ATP (5,000 Ci/mmol) based on a peptide substrate described in Terada et al, *J. Biol. Chem.* 268: 12062–8 (1993), in 30 µl, one aliquot was analyzed for the amount of recombinant pp70 S6 kinase in the precipitate. After 25 minutes at 22° C. the reaction was stopped by the addition of 10 µl of 500 mM EDTA. Twenty two µl of the supernatant was applied to phosphocellulose paper P81 made by Whatman Products, Fisher Scientific, Pittsburg, Pa., and washed four times in 75 mM $H_3PO_4$. The relative amounts of incorporated radioactivity was determined in a liquid scintillation counter. Specific phosphorylation of the S6-derived peptide was obtained after subtracting counts with protein A-Sepharose beads in the absence of anti-HA-antibody from counts of label incorporated in the presence of anti-HA-antibody.

For all the other kinase assays, one-third of the immuno-beads were subjected to an in vitro kinase reaction, and two-thirds were analyzed for the amount of the respective recombinant kinase protein. For analyzing Akt kinase activity histone H2B was used as substrate as described in Franke et al., *Cell* 81:727–36 (1995), according to the reaction conditions described by Jones et al, *PNAS USA* 88:4171–5 (1991). JNK-activity was determined using GST-Jun (amino acids of Jun 1 through 89, which a slight variation from a standard version that contains amino acids 1 through 79) as a substrate as described in Derijard et al., *Cell* 76:1025–37 (1994). For MAP kinase activation, the phosphorylation of myelin basic protein (MBP) was analyzed as described by Ray et al., *PNAS USA* 85:3753–7 (1988). The in vitro protein kinase reactions were carried out in 30 µl in the presence of [y-$^{32}$p] ATP (5,000 Ci/mmol) and incubated at 22° C. for 25 minutes. The reactions were stopped by the addition of 8 µl Lammli-sample buffer and 22 µl of the reaction mixtures were analyzed by SDS-PAGE. The relative amounts of incorporated radioactivity was determined by autoradiography and quantitated using a Molecular Imager System produced by BioRad, Richmond, Calif. The complexes were analyzed by immunoblotting with the indicated antibodies.

The presence of PI 3-kinase activity in immune complexes was determined by incubating the beads with 30 mM HEPES, 30 mM $MgCl_2$, 50 µM ATP, 200 µM adenosine, 0.2 mg sonicated PI per ml and 10 µCi [$\lambda$-$^{32}$P] ATP (5,000 Ci/mmol) for 20 minutes at 25° C. Adenosine was added to inhibit any contaminating PI 4-kinase activity as described Whitman et al., *Nature* 332:644–6 (1988). Reactions were stopped by adding 100 µl of 1M Hcl and the phospholipids were extracted with 200 µl of a 1:1 mixture of chloroforn The reaction products were separated by thin layer chromatography as previously described in Kaplan et al., *PNAS USA* 83:3624–8 (1986). The conversion of PI to PI 3-phosphate was determined by autoradiography.

In addition, phosphoprotein 70 (pp70 ) S6 kinase activation by coexpression of the polynucleotide sequences with pp70 S6 kinase was demonstrated. The indicated Myc-tagged polynucleotide sequences were coexpressed with HA-tagged pp70 S6 kinase. p110 kinase or p110* kinase with either a myristoylation (M) cell membrane targeting sequence added to the N-terminus, or a famesylation and palmitoylation sequence (H) cell membrane targeting sequence added to the C-terminus resulted in increased levels of pp70 S6 kinase activity. pp70 S6 kinase is a known downstream effector of PI 3-kinase.

EXAMPLE 4

Fly Eye Screen for Inhibitors of PI 3-Kinase Activity

In this example, p110* expressing Drosophila melanogaster is created for use as a screen for PI 3-kinase inhibitors.

p110*, a growth factor independent PI 3-kinase mutant is expressed in the developing eye tissue of the fruit fly Drosophila melanogaster, using the GMR promoter described in Hay et al., *Development* 120:2121–9 (1994). The expression of p110* under the control of the eye specific promoter leads to developmental defects which result in obvious aberrations in the external morphology of the external eye tissue. The mutant morphology that results in the transgenic flies is called "rough" eye. "Rough eye" morphology is a fly eye with aberrant morphology that is detectable under a dissecting microscope. These defects may depend on PI 3-kinase activity, as indicated by a control experiment transforming developing flies with a PI 3-kinase mutant that contains a mutated kinase domain. The fly eye cells transformed with a catalytically inactive PI 3-kinase mutant are incapable of eliciting the rough eye morphological effects of the catalytically active counterpart.

The results of the transformation of the developing fly tissue result in ectopic production of R7 photoreceptor cells is observed in p110* expressing eyes of the Drosophila, which is a phenotype characteristic of the activation of the Ras signaling molecule. Thus, as in mammalian cells, p110* appears to activate Ras in Drosophila tissue and indeed mutations that reduce Ras activity in Drosophila, reduce the phenotypic effects of p110*. Even with this information, the invention is not limited to any theories of mechanism of how the invention works.

Drosophila embryos are transformed by the method described in Karess and Rubin, Cell 38:135–146 (1984) with a polynucleotide construct made up of a p110* coding sequence under the regulatory control of a GMR promoter. The flies are allowed to develop normally and are selected by eye morphology for successful transformants. Successful transformants will have a rough eye morphology. The transgenic flies are then fed food spiked with an appropriate dose of a candidate inhibitor. The amount of the inhibitor will depend on the deduced possible potency of the molecule as an inhibitor. In this case, the flies are fed different small molecule inhibitors; a different inhibitor is selected for each population of transformants. The flies are fed a candidate inhibitor throughout third instar development during which time they are observed for reversions of their eye morphology to wild type or normal. Positives are identified and the inhibitors are then retested by this assay, or by a kinase or binding assay. This screening method may also be applied as a secondary or tertiary screen using candidate inhibitors that have already been found positive in prior screens such as the kinase or binding assay screening protocols.

Alternative screens are conducted by injecting a candidate inhibitor into the third instar larvae of the transformants that are then observed for a reversion of the rough eye morphology to normal.

EXAMPLE 5

Inducible Expression System for PI 3-kinase Mutant p110*

Expression of inducible p110* was achieved fusing the coding region for p110* with the GR525 mutant of the regulatory domain of the mouse estrogen receptor (ER) as described in Littlewood et al., *Nucleic Acids Research* 23:1686–1690 (1995). Activation is regulated by the addition of 4-hydroxy tamoxifen (4-OHT), a natural breakdown product of estrogen: in the presence of 4-OHT the p110*-ER chimera is activated. The respective expression vector was further modified by addition of the 5' untranslated leader sequence from the Herpes simplex virus tk-gene to provide for efficient translation initiation of p110*.

With the ability to regulate p110* activity it is possible to generate stable cell lines, since in the uninduced state of the system background activity of p110 * is kept low. Pathways induced by PI 3-kinase can be studied simply by 4-OHT to the culture medium. Time-course experiments after induction give information about the successive order (early/late) and the duration of the respective responses. An inducible expression system for p110* will aid in the determination of whether activation of PI 3-kinase is sufficient for a mitogenic response and/or anchorage-independent cell growth. Using this system allows us to address several key questions about the importance of PI 3-kinase activation for the regulation of cell growth and mitogenesis. After inducing PI 3-kinase activity by 4-OHT we found that activation of PI 3-kinase is sufficient for a mitogenic response as measured by incorporation of radiolabeled thymidine (DNA synthesis) and for anchorage-independent cell growth as analyzed by colony formation in soft agar.

Additionally, the 4-OHT -regulatable expression system is reversible, so that p110* expression can be switched on and off. Regulatable expression of constitutively active forms of PI 3-kinase is an ideal system to identify genes that are induced in response to PI 3-kinase activation. This can be achieved either by subtractive hybridization or by differential display after MRNA isolation from cells grown in the absence or presence of 4-OHT.

EXAMPLE 6

Production of PI 3-kinase Induced Phospholipids and Their Direct Activation of Akt $PI3,4P_2$ activates Akt in a defined phospholipid vesicle system in vitro as described in Klippel et al., *Mol. Cell. Biol.* 16(8):4117–4127 (1996). To optimize reaction conditions commercially available synthetic PI3P and $PI3,4P_2$ dipalmitoyl derivatives were tested for in vitro Akt stimulation. Phospholipid vesicles were prepared containing dipalmitoylated PI3P or dipalmitoylated $PI3,4P_2$, PI4P and phosphatidylserine (PS), phosphatidylcholine (PC), phosphatidylethanolamine (PE), or combinations of these as described previously to mimic their relative concentrations found in cells. The phospholipid vesicles were preincubated with immobilized Akt protein. The kinase activity of Akt was analyzed by an in vitro kinase assay using histone H2B as substrate. In this system $PI3,4P_2$ in PC vesicles induced an approximately 2.5 fold increase in kinase activity of Akt. No activation was observed with $PI3,4P_2$ in either PE or PS vesicles. Conditions using PE/PS vesicles that were shown to promote in vitro activation of $Ca^{2+}$-independent PKC isoforms by $PI3,4P_2$ and $PI3,4,5P_3$ did not allow activation of Akt. The presence of PS in the $PI3,4P_2$/PC vesicles interfered with Akt activation, whereas certain concentrations of PE were tolerated. No stimulation of Akt kinase activity was observed with vesicles containing PI3P under any conditions. An aliquot of each immunocomplex was analyzed in parallel for protein levels. No further increase in Akt activation using synthetic dipalmitoyl derivatives of $PI3,4P_2$ at concentrations ranging from 260 nM to 1.3 $\mu$M was observed. Next we established a system in which all 3' phosphorylated inositol phospholipids generated by PI 3-kinase could be analyzed in vitro.

We observed that Akt activation in vitro by a constitutively active PI 3-kinase is mediated by $PI3,4P_2$. To generate the known cellular products of PI 3-kinase, PI3P, $PI3,4P_2$ and $PI3,4,5P_3$, and to compare these products with other phospholipids for the activation of Akt in vitro, we used the constitutively active PI 3-kinase, p110*. We have also showed that p110* and its derivatives exhibit high specific enzymatic activities in vitro and can efficiently induce signaling events when expressed in mammalian cells, as described earlier. p110* was extended at the C-terminus with six histidine residues (p110*.6His), expressed in Sf9 insect cells, and purified on a Ni-chelating column. To generate 3' phosphorylated inositol phospholipids in vitro purified p110* was incubated in the presence of ATP with the PI 3-kinase substrates PI, PI4P or $PI_{4,5}P_2$, each in vesicles containing phosphatidylcholine (PC). A fraction of each sample was subjected to phospholipid extraction and analyzed for production of PI3P, $PI3,4P_2$ and $PI3,4,5P_3$. Approximately 5% to 10% of the substrates were converted into 3' phosphorylated inositol phospholipids under these conditions. In order to. assess the ability of these lipids to stimulate Akt, phospholipid vesicles were preincubated with Akt. The kinase activity of Akt was analyzed in an in vitro kinase assay using histone H2B as substrate. Although comparable amounts of all three 3' phosphorylated inositol phospholipid products had been generated, only Akt molecules that were preincubated with vesicles containing $PI3,4P_2$ exhibited a substantial increase in kinase activity. Control samples containing either untreated phospholipid vesicles or p110* only failed to activate Akt. The addition of 1 PM $PI3,4P_2$ resulted in an average of 3-fold stimulation of Akt. A greater degree of stimulation (9 fold) was observed at higher concentration (4 $\mu$M) of $PI3,4P_2$. In parallel half of the Akt immunocomplexes were analyzed by Western-blotting to insure equal protein concentration in all samples. Akt did not appear to be activated through direct phosphorylation by the protein kinase activity of p110*, since the presence of p110* protein per se did not result in increased Akt kinase activity. p110* was an active protein kinase under the reaction conditions employed, since its autophosphorylation could be detected. Under the same conditions no Akt phosphorylation was detected. Additional control samples in which p110* was added to phospholipid vesicle substrates immediately before incubation with Akt, did not show activation of Akt. This suggests that $PI3,4P_2$ has to accumulate at sufficiently high concentration in the PI 3-kinase reaction before Akt activation can be observed. These results demonstrate that it is possible to reconstitute PI 3-kinase-mediated activation of Akt in vitro with defined components and that Akt is an immediate downstream effector of PI 3-kinase. Furthermore, they suggest that the PI 3-kinase produced phosphatidylinositides can act as second messengers.

Akt-kinase activation was demonstrated by coexpression of p110 derivatives. Myc-tagged p110 molecules were coexpressed with HA-tagged Akt-kinase. p110 kinase or p110* kinase with either a myristoylation (M) cell membrane targeting sequence added to the N-terminus or a farnesylation and palmitoylation sequence (H) cell membrane targeting sequence added to the C-terminus in the case of a farnesylation and palmitoylation resulted in increased levels of AKT kinase activity. AKT kinase is a known downstream effector of PI 3-kinase.

In addition, in vitro stimulation of Akt by p110*-generated $PI3,4P_2$ was demonstrated. The PI 3-kinase substrates PI, PI4P and $PI_{4,5}P_2$ in PC vesicles were phosphorylated by purified p110* protein in the presence of ATP (with 2500 cpm/pmol [g-$^{32}$P]ATP) to obtain PI3P, $PI3,4P_2$ and $PI3,4,5P_3$. In order to monitor the production of phosphatidylinositides by p110* a fraction of each reaction was subjected to phospholipid extraction. The lipids were resolved by thin-layer chromatography (TLC) and visualized by autoradiography. The amount of labeled phospholipid products was quantitated by scraping the respective areas of the TLC plate and counting in a scintillation counter. The in vitro assay for activation of Akt by $PI3,4P_2$. was conducted using the phospholipid vesicles prepared as just described, mixed with Akt for 10 min. Subsequently, the kinase activity of Akt was assayed as described above. The following reaction conditions were tested: Akt was incubated with reaction buffer alone, with reaction buffer containing PI, PI4P or $PI4,5P_2$ phospholipid vesicles, and with PI, PI4P or $PI4,5P_2$ phospholipid vesicles that had been treated with p110*; 1 and 4 $\mu$M of each PI 3-kinase product were tested, respectively. As additional controls, Akt was incubated in mixed vesicles, then p110* was added and Akt was incubated with p11 * protein in the absence of phospholipid vesicles. In samples containing phospholipid vesicles the total lipid concentration was maintained at approximately 1000 $\mu$M. The 3' phosphorylated inositol phospholipids were presented in an excess of PI, PI4P or $PI3,4P_2$ (80 to 100 $\mu$M) and PC (800 to 900 $\mu$M). Relative amounts of Akt were analyzed by immunoblotting. An aliquot of each immunocomplex was analyzed in parallel for protein levels by Western-blotting with anti-Akt antibody. Akt kinase activities were quantitated using a Molecular Imager (BioRad). The increase in Akt kinase activity is expressed relative to samples containing unstimulated Akt.

We determined that the PH domain at the Akt N-terminus is essential for $PI3,4P_2$ mediated stimulation. It has previously been reported that the stimulation of the kinase activity of Akt by PI 3-kinase in vivo is dependent on the PH domain at its immediate N-terminus. We determined that $PI3,4P_2$ mediates its stimulatory effect on Akt through its PH domain by introducing a point mutation in the PH domain of Akt (Akt RC25) which abrogates PI 3-kinase-mediated Akt activation in vivo. A kinase-deficient Akt, Akt KA179, was tested as an additional control. We incubated Akt, Akt RC25 and Akt KA179 proteins with $PI3,4P_2$ in phospholipid vesicles using p110* as described above. Akt was efficiently activated by $PI3,4P_2$ containing vesicles, while Akt RC25 was not activated. The basal kinase activity of Akt RC25 remained unaffected under the same conditions suggesting that the RC25 mutation in the PH domain does not interfere with basic kinase function, but rather affects the ability of the mutant Akt molecules to become activated. The kinase-deficient Akt KA179 had no detectable enzymatic activity.

COS-7 cells were obtained from the American Type Culture Collection and cultured at 37° C. in Dulbecco's modified Eagle medium containing 10% bovine calf serum, penicillin (50 $\mu$g/ml) and streptomycin (50 $\mu$g/ml). *Spodopterafrugiperda* (Sf9) cells (from M. Summers, Texas A&M University, College station) were grown in ISFM-7 medium. Recombinant baculovirus expressing p110*.6His was prepared from the supernatant of Sf9 cells as described previously.

Ascites fluid with the murine anti-influenza virus hemagglutinin 1 (HA1) monoclonal antibody 12CA5 and hybridoma 9E10 are available commercially and using these mouse ascites fluid containing murine monoclonal anti-Myc antibody was prepared. Rabbit polyclonal anti-Akt/RAC-PK antibody is also commercially available. Rabbit polyclonal anti-SHC antiserum has been described.

The mammalian expression vectors for the HA-tagged kinase Akt/RAC-PK and Akt RC25 were described previously The cDNA for Akt/Rac KA179 was cloned into the same expression vector as wt Akt.

To generate p110*.6His the C-terminal end of p110 was modified using primer 6-His-sense-(5'GC GCC CAC CAT CAT CAC CAC CAT TGA GTC GAC G) SEQ ID NO.1 and primer 6His-antisense-(5'GA TCC GTC GAC TCA ATG GTG GTG ATG ATG GTG G) SEQ ID NO. 2 flanked by restriction sites for Kas I and Bam HI. The 6His coding region was attached in frame to the p110 C-terminus by ligating the annealed oligonucleotide via Kas I-Bam HI ends into pCG-p110H. This extended the p110 C-terminal end by a sequence encoding amino-acids DLGGA (SEQ ID NO. 3) as a hinge region (overlapping restriction sites SacI/Ecl136II and KasI/NarI), which precedes the coding region for the six histidine residues, a stop-codon and a BamHI restriction site.

For expression in insect cells the coding region for pI 10*.6His was reconstituted using p110.16His and DNA fragments from previously described p110* constructs and cloned into baculovirus expression vector pVL 1392 (available from Pharmingen) via XbaI-BamHI ends.

p110*.6His was transiently expressed in insect cells Sf9 cells were infected with recombinant baculovirus directing the expression of p110*.6His protein. The cells were harvested after 50 h by centrifugation at 1000×g, washed with ice-cold PBS and lysed at 4° C. in lysis buffer containing 20 mM Tris (pH 7.5), 137 mM NaCl, 15% (vol/vol) glycerol, 1% (vol/vol) Triton X-100, 2 mM EDTA, 2 mM phenylmethylsulfonyl fluoride, 10 mg aprotinin per ml, 20 mM leupeptin, 2 mM benzamidine. Lysates were cleared by centrifugation at 14,000×g for 5 minutes. The Sf9 cell extract was loaded on a 1×7 cm Ni-chelating chelating Sepharose FF column equilibrated in buffer A (20 mM HEPES [N-2-hydroxyethyl-piperazine-N'-2-ethanesulfonic acid, pH 7.5], 150 mM NaCl, 20 mM imidazole [pH 7.5], 5 mM b-mercaptoethanol, 10% [vol/vol] glycerol) containing 0.5% Triton X-100. The column was washed in buffer A and developed with a 20 to 200 mM gradient of imidazole in buffer A. Fractions containing purified pI 10*.6His protein (100 to 200 µg/ml) were pooled.

For preparing GST-SIP-110 protein the coding region of SIP-110 was expressed in insect cells as GST-fusion using the baculovirus expression vector pVIKS. The cells were lysed as described above and SIP-110 was immobilized by binding to GST-agarose according to manufacturer's instructions (Pharmacia, located in New Jersey). Alternatively SIP was immunoprecipitated from stimulated B-cell lysates using anti-SHC antibodies as described earlier. Akt/ RAC-PK/PKB was transiently expressed in COS-7 cells. COS cells (60 to 70% confluent on a 10 cm plate) were transfected with mammalian expression vectors encoding HA-tagged Akt, Akt RC25 or Akt KA179 using the DEAE-dextran method. Cells were starved for 36 hours. COS cells were washed twice with cold phosphate-buffered saline and lysed at 4° C. in 20 mM Tris (pH 7.5), 137 mM NaCl, 15% (vol/vol) glycerol, 1% (vol/vol) Triton X-100, 2 mM EDTA, 2 mM phenylmethylsulfonyl fluoride, 10 mg aprotinin per ml, 20 mM leupeptin and 2 mM benzamidine. Lysates were cleared by centrifugation at 14,000×g for 5 minutes. Cell-lysates containing HA-tagged Akt were incubated with monoclonal anti-HA antibody 12CA5 for 1 h at 4° C. Protein A-Sepharose beads (Sigma) were used to precipitate the immunocomplexes. The beads were washed with 50 mM Tris-HCl (pH 7.5), 0.5 M LiCl, 0.5% (vol/vol) Triton X-100, twice with PBS and once with 10 mM Tris-HCl (pH 7.5), 5 mM b-glycerolphosphate, 2 mM dithiothreitol. Half of the immunobeads was subjected to an in vitro kinase reaction, the second half was analyzed for the amount of protein by immunoblotting.

Phospholipid mixes containing phosphatidyl-serine (PS), phosphatidylcholine (PC) or phosphatidylethanolamine (PE) (Avanti Polar Lipids, Sigma) as carriers were dried under a stream of nitrogen and sonicated (at 2 mg/ml) in 50 mM HEPES (pH 7.2) using a bath sonicator. To generate vesicles containing synthetic 3' phosphorylated phosphatidylinositides the sonication was carried out in the presence of dipalmitoylated PI3P or PI3,4P$_2$ (Matreya). Alternatively, vesicles containing the PI 3-kinase substrates PI, PI4P or PI$_{4,5}$P$_2$ (Avanti Polar Lipids, Boehringer Mannheim) were treated with purified p110*. The lipids were incubated with p110*.6His protein (10 µg/ml) in 50 mM HEPES (pH 7.2), 5 mM MgCl2, 50 pLM [g-$^{32}$P]ATP (2500 cpm/pmol) and 2 mM dithiothreitol. A typical reaction mix contained 80 to 100 µM PI, PI4P or PI4,5P$_2$ and 880 µM PC Under these conditions approximately 5% to 10% of the substrates were converted into 3' phosphorylated phosphatidylinositides.

The reaction conditions employed were not optimal for the PI 3-kinase reaction, but allowed for maximal Akt stimulation in the subsequent protein kinase assay (see below). The phospholipid reactions were either used directly in the Akt kinase assay or were stopped by the addition of an equal volume of 1 M HCl and extracted using twice the volume of methanol/chloroform (1:1). Extracted lipids were dried and stored at −75° C. or sonicated in reaction buffer and subjected to treatment with immobilized preparations of SIP proteins on glutathione- or immunobeads. The generation/ conversion of 3' phosphorylated phosphatidylinositides was monitored using a fraction of the respective reactions. Reaction products were extracted and separated by thin layer chromatography (TLC) using H20, acetic acid, methanol, acetone and chloroform(14:24:26:30:80 [vol/vol]) The production of PI3P, PI3,4P$_2$ and PI3,4,5P$_3$ wa visualized by autoradiography. PI, PI4P and PI4,5P$_2$ in the reaction mixture served as internal standards and were visualized after staining in iodine-vapor. Labeled phospholipid products were quantitated by scraping the respective areas of the TLC plate and counting in a scintillation counter. The amounts of PI3P, PI3,4P$_2$ and PI3,4,5P$_3$ produced were calculated based on the specific activity of the [g-$^{32}$P]ATP used.

The assay for the in vitro protein kinase activity of Akt was conducted with immobilized Akt that was preincubated with or without mixed phospholipid vesicles (20 µl) for 10 min and subjected to an in vitro protein kinase assay using histone H2B (Boehringer Mannheim) as a substrate. The reactions were carried out in 30 µl at 22° C. for 20 min in the presence of 5 µCi [g-$^{32}$P]ATP. The reactions were stopped by the addition of 8 µl Lammli-sample buffer and 22 µi of each reaction mixture were analyzed by 16% SDS-PAGE. The relative amounts of incorporated radioactivity were visualized by autoradiography and quantitated using a Molecular Imager System (BioRad).

Immunoprecipitates were boiled in Laml i-sample buffer, separated by SDS-PAGE and transferred to nitrocellulose-filters (Schleicher & Schuell). Filters were blocked in TBST buffer (10 mM Tris-HCl [pH 7.5], 150 mM NaCl,.0.05% (vol/vol) Tween 20, 0.5% (wt/vol) sodium azide) containing 5% (wt/vol) dried milk. Antibodies were added in TBST at appropriate dilutions. Bound antibody was detected with anti-mouse or anti-rabbit conjugated to alkaline phosphatase (Promega, located in Madison, Wis.) in TBST, washed, and developed with nitroblue tetrazolium and 5-bromo-4-chloro-3-indolyl phosphate (Promega).

EXAMPLE 7

Method of Treating Cell Death From Trauma

A patient is diagnosed with having had a stroke. The site of the affected tissue in the brain is determined. A gene therapy vehicle is prepared with a nonviral vector and a polynucleotide sequence having a p110 subunit sequence, an iSH2 sequence, a linker sequence and a myristoylation encoding sequence for membrane attachment. This sequence is delivered in the vehicle to the patient at the site of brain tissue damage. Cell death from the trauma is thereby reduced.

EXAMPLE 8

Method of Treating Cell Death From Heart Attack Trauma

A patient is diagnosed with having had a heart attack, and an ischemic lesion in the heart is identified. Vesicles containing 3' phosphorylated inositol phospholipids made in cells expressing membrane targeted p110* polynucleotides are administered by catheter to the region of the heart having the ischemic lesion, thereby restoring some of the cells from loss due to the trauma.

EXAMPLE 9
Method of Promoting Activation of Insulin Signaling Pathway

A patient having reduced responsiveness to insulin in cells that would normally be expected to be responsive to insulin where glucose has been released, for example after a meal, is administered a viral-based gene therapy vehicle having a polynucleotide of the invention systemically, in the portal vein, targeting the liver organ. The gene therapy vehicle provides expression in cells of a membrane targeted PI 3-kinase mutant of the invention, providing activation of insulin signaling in the non-responsive cells, or cell exhibiting a reduced responsiveness to insulin.

What is claimed is:

1. A transgenic fly comprising a transgene having a polynucleotide sequence comprising:
   (a) a first nucleotide sequence comprising a sequence selected from the group consisting of:
      (i) a nucleotide sequence encoding the p110 subunit of a mammalian PI 3-kinase protein, and
      (ii) a nucleotide sequence encoding a derivative or mutant of (a)(i) having single or multiple nucleotide substitutions, deletions or additions, said nucleotide encoding said derivative or mutant of (a)(i) having at least 50% identity to a native nucleotide sequence encoding p110, said derivative or mutant having 60–95% sequence identity to the native amino acid sequence of the p110 subunit of PI 3-kinase and an activity of the p110 subunit of mammalian PI 3-kinase;
   (b) a second nucleotide sequence comprising a sequence selected from the group consisting of:
      (i) a nucleotide sequence encoding the iSH2 domain of the p85 subunit of PI 3-kinase protein which binds the p110 subunit of a mammalian PI 3-kinase protein, and
      (ii) a nucleotide sequence encoding a derivative or mutant of (b)(i) having single or multiple nucleotide substitutions, deletions or additions, said nucleotide sequence encoding said derivative or mutant of (b)(i) having at least 80% nucleotide sequence identity to (b)(i), said derivative or mutant binding the p110 subunit of a mammalian PI 3-kinase protein, wherein said second nucleotide sequence is attached to a linker nucleotide sequence encoding a linker, said linker nucleotide sequence being attached to the 5' end of said first nucleotide sequence and forming a first fusion sequence; and
   (c) a third nucleotide sequence encoding a cell membrane targeting sequence, wherein said third nucleotide sequence is attached to the 5' or 3' end of said first fusion sequence, wherein said polynucleotide sequence is under regulatory control of an eye specific promoter, wherein expression of said transgene in said fly results in a phenotypic change in eye morphology from normal to rough eye morphology, wherein said fly is a species of Drosophila.

2. A method of screening for an inhibitor of PI 3-kinase comprising:

(a) administering a candidate inhibitor to the transgenic fly of claim 1, and (b) observing any reversion in phenotype to normal eye morphology in said fly, said reversion being indicative of PI 3-kinase inhibitor activity.

3. The transgenic fly of claim 1, wherein said cell membrane targeting sequence is selected from the group consisting of:

(a) a myristoylation cell membrane targeting sequence; and (b) farnesylation and palmitoylation cell membrane targeting sequences.

4. The transgenic fly of claim 3, wherein said first fusion sequence consists of a nucleotide sequence encoding p110*.

* * * * *